United States Patent [19]
Weigl et al.

[11] Patent Number: 5,948,684
[45] Date of Patent: *Sep. 7, 1999

[54] SIMULTANEOUS ANALYTE DETERMINATION AND REFERENCE BALANCING IN REFERENCE T-SENSOR DEVICES

[75] Inventors: Bernhard H. Weigl; Mark R. Holl; Diane Zebert, all of Seattle; Margaret Kenny, Edmonds; Caicai Wu, Seattle, all of Wash.

[73] Assignee: University of Washington, Seattle, Wash.

[ * ] Notice: This patent is subject to a terminal disclaimer.

[21] Appl. No.: 08/900,926

[22] Filed: Jul. 25, 1997

Related U.S. Application Data

[63] Continuation-in-part of application No. 08/829,679, Mar. 31, 1997, and a continuation-in-part of application No. 08/625,808, Mar. 19, 1996, Pat. No. 5,716,852.

[51] Int. Cl.$^6$ .................................................. G01N 35/08
[52] U.S. Cl. .............................. 436/52; 436/53; 436/172; 436/177; 436/180; 422/81; 422/82; 422/82.08
[58] Field of Search ..................................... 436/172, 177, 436/180, 52, 53; 422/81, 82, 82.08

[56] References Cited

U.S. PATENT DOCUMENTS

| | | | |
|---|---|---|---|
| 3,449,938 | 6/1969 | Giddings | 73/23.39 |
| 3,795,489 | 3/1974 | Warnick et al. | 422/52 |
| 4,147,621 | 4/1979 | Giddings | 210/637 |
| 4,214,981 | 7/1980 | Giddings | 209/155 |
| 4,250,026 | 2/1981 | Giddings et al. | 209/155 |
| 4,683,212 | 7/1987 | Uffenheimer | 436/52 |
| 4,726,929 | 2/1988 | Gropper et al. | 422/82.04 |
| 4,737,268 | 4/1988 | Giddings | 209/12.2 |

(List continued on next page.)

FOREIGN PATENT DOCUMENTS

| | | |
|---|---|---|
| 0 294 701 B1 | 12/1988 | European Pat. Off. . |
| 0 381 501 A2 | 8/1990 | European Pat. Off. . |
| 0 645 169 A1 | 3/1995 | European Pat. Off. . |

(List continued on next page.)

OTHER PUBLICATIONS

Brody et al. *Proc. SPIE–Int. Soc. Opt. Eng.* vol. 2978, pp. 103–110, 1997.

(List continued on next page.)

*Primary Examiner*—Maureen M. Wallenhorst
*Attorney, Agent, or Firm*—Greenlee, Winner and Sullivan, P.C.

[57] ABSTRACT

A reference T-sensor system is provided for detecting the presence and/or measuring the concentration of analyte particles in a sample stream. The system includes: a) a laminar flow channel; b) three or more inlet means in fluid connection with the laminar flow channel for respectively conducting into the laminar flow channel (1) an indicator stream which may include an indicator substance which indicates the presence of the analyte particles, (2) the sample stream, and (3) a reference stream, which can be a control stream and/or internal standard stream; c) wherein the laminar flow channel has a depth and/or width sufficiently small to allow laminar flow of the streams and a length sufficient to allow particles of the analyte to diffuse into the indicator stream to form a detection area; and d) outlet means for conducting the streams out of the laminar flow channel preferably to form a single mixed stream. Also provided are methods of using the device to improve accuracy and increase convenience of measuring the concentration of analytes in a sample. Monitoring reference stream(s) in laminar flow with sample stream(s) allows for calibration or for monitoring or correcting for the effects of experimental conditions which might otherwise degrade accuracy. A reference stream which serves as both a control stream and an internal standard stream is convenient and economical. The device of this invention also needs less frequent calibration than previously-known fluid analysis devices because the devices and methods of this invention provide for continuous and simultaneous quality control and internal standardization.

20 Claims, 12 Drawing Sheets

U.S. PATENT DOCUMENTS

| | | |
|---|---|---|
| 4,756,884 | 7/1988 | Hillman et al. .............................. 422/73 |
| 4,830,576 | 5/1989 | Giddings .................................. 210/239 |
| 4,894,146 | 1/1990 | Giddings .................................. 209/12.2 |
| 4,908,112 | 3/1990 | Pace ....................................... 210/198.2 |
| 4,983,038 | 1/1991 | Ohki et al. ............................... 356/246 |
| 5,039,426 | 8/1991 | Giddings .................................. 210/748 |
| 5,141,651 | 8/1992 | Giddings .................................. 210/748 |
| 5,156,039 | 10/1992 | Giddings ................................ 73/865.5 |
| 5,193,688 | 3/1993 | Giddings .................................. 209/155 |
| 5,240,618 | 8/1993 | Caldwell et al. ......................... 210/748 |
| 5,250,263 | 10/1993 | Manz ........................................ 422/81 |
| 5,288,463 | 2/1994 | Chemelli .................................. 422/58 |
| 5,304,487 | 4/1994 | Wilding et al ............................ 435/29 |
| 5,389,524 | 2/1995 | Larsen et al. ............................. 435/29 |
| 5,465,849 | 11/1995 | Wada et al. .............................. 209/214 |
| 5,480,614 | 1/1996 | Kamahori ................................. 422/70 |
| 5,599,432 | 2/1997 | Manz et al. .............................. 204/451 |
| 5,599,503 | 2/1997 | Manz et al. .......................... 422/82.05 |
| 5,635,358 | 6/1997 | Wilding et al. .......................... 435/7.2 |
| 5,637,469 | 6/1997 | Wilding et al. ......................... 435/7.21 |
| 5,716,852 | 2/1998 | Yager et al. ............................. 436/172 |
| 5,726,751 | 3/1998 | Altendorf et al. ...................... 356/246 |
| 5,747,349 | 5/1998 | van den Engh et al. ............... 436/172 |

FOREIGN PATENT DOCUMENTS

| | | |
|---|---|---|
| WO 93/22053 | 11/1993 | WIPO . |
| WO 96/04547 | 2/1996 | WIPO . |
| WO 96/12541 | 5/1996 | WIPO . |
| WO 96/15576 | 5/1996 | WIPO . |
| WO 97/00125 | 1/1997 | WIPO . |
| WO 97/02357 | 1/1997 | WIPO . |

OTHER PUBLICATIONS

Brody, J.P. and Yager, P. (1996), "Low Reynolds Number Micro–Fluidic Devices," Solid State Sensor & Actuator Workshop, Hilton Head, SC, Jun. 2–6, 1996 pp. 105–108.

Faucheux, L.P. et al. (1995), "Optical Thermal Ratcher," Phys. Rev. Lett. 74:1504–1507.

Giddings, J.C. (1985), "Optimized Field–Flow Fractionation System Based on Dual Stream Splitters," Anal. Chem. 57:945–947.

Giddings, J.C. et al. (1983), "Outlet Stream Splitting for Sample Concentration in Field–Flow Fractionation," Separation Science and Technology 18(3):293–308.

Giddings, J.C. (1993), "Field–Flow Fractionation: Analysis of Macromolecular, Collodial and Particulate Materials," Science 260:1456–1465.

Leff, H.S. and Rex, A.F. (1990) "Resource letter MD–1: Maxwell's demon," Am. J. Phys. 58::201–209.

Manz, A. et al. (1993) "Planar Chips Technology for Miniaturization of Separation Systems: A Developing Perspective in Chemical Monitoring," Advances in Chromatography 33:2–66.

Petersen, K.E. (1982) "Silicon as a Mechanical Material," Proc. IEEE 70(5):420–457.

Reisman, A. et al. (1979) "The Controlled Etching of Silicon in Catalyzed Ethylendiamine–Pyrocatechol–Water Solutions," J. Electrochem. Soc.126:1406–1415.

Rousseler, J. et al. (1994) "Directional motion of brownian particles induced by a periodic asymmetric potential," Nature 370:446–448.

Shoji, S. and Esashi, M. (1994) "Microflow devices and systems,"J. Micromech and Microeng. 4:157–171.

Verpoorte, E.M.J. et al. (1994) "Three–dimensional micro flow Manifolds for miniaturized chemical analysis systems," J. Micromech. Microeng. 4:246–256.

Wallis, G. and Pomerantz, D.I. (1969) "Field Assisted Glass–Metal Sealing," J. Appl. Phys. 40:3946–3949.

Weigl, B.H. and Yager, P. (1996) "Silicon–Microfabricated Diffusion–Based Optical Chemical Sensor," presented at Europtrode Conference, Zurich, Switzerland, Apr. 2–3,1996.

Weigl, B.H. et al. (1997) "Fluorescence and absorbance analyte sensing in whole blood and plasma based on diffusion separation in silicon–microfabricated flow structures, " SPIE Proceedings, J. Lakowitz (ed), Fluorescence Sensing Technology III (Feb. 9–11, 1997).

Weigl, B.H. et al. (1996) "Diffusion–Based Optical Chemical Detection in Silicon Flow Structures," Analytical Methods & Instrumentation Special Issue TAS 96 (Nov. 1996) pp. 174–784.

Weigl, B.H. et al. (1996) "Rapid sequential chemical analysis in microfabricated flow structures using multiple fluorescent reporter beads," TAS 96 (Nov. 1996).

Williams, P.S. et al. (1992) "Continous SPLITT Fractionation Based on a Diffusion Mechanism," Ind. Eng. Chem. Res. 31:2172–2181.

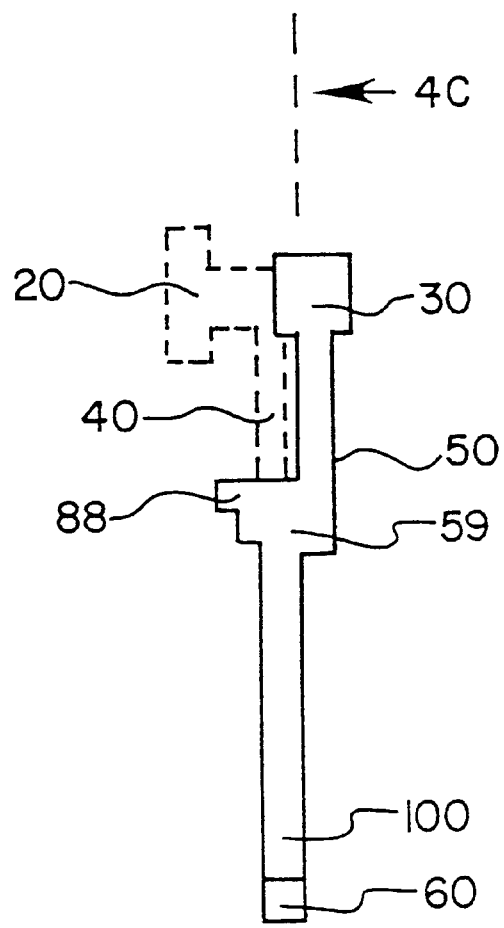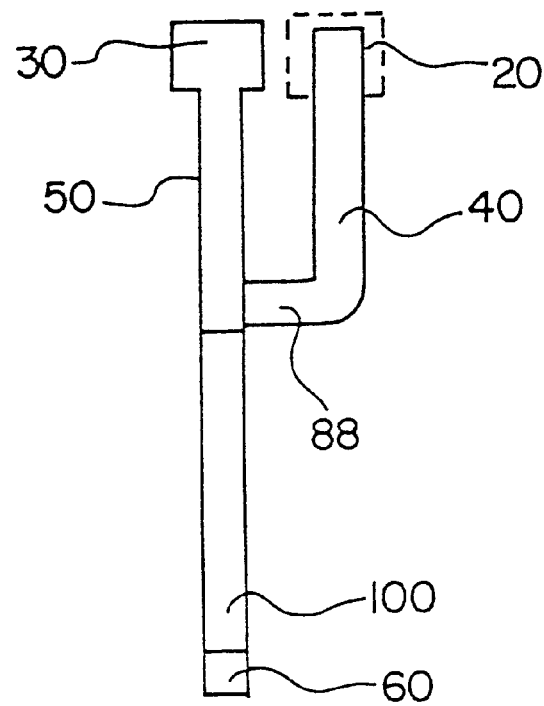
Fig. 4B
Fig. 4C

SIMULTANEOUS ANALYTE DETERMINATION AND REFERENCE BALANCING IN REFERENCE T-SENSOR DEVICES

CROSS-REFERENCE TO RELATED APPLICATIONS

This application is a continuation-in-part of Ser. No. 08/625,808, filed Mar. 31, 1997, now U.S. Pat. No. 5,716, 852 issued on Feb. 10, 1998, and application Ser. No. 08/829,679, filed Mar. 31, 1997 incorporated herein by reference to the extent not inconsistent herewith.

BACKGROUND OF THE INVENTION

In Maxwell's famous Gedanken (thought) experiment, a demon operates a door between two boxes of gas at the same temperature. The demon sorts the molecules keeping the faster molecules in one box and the slower in the other, violating the basic laws of thermodynamics. This paradox has since been resolved in many different ways. Leff, H. S. and Rex, A. F. (1990), "Resource letter md-1: Maxwell's demon," Am. J. Physics 58:201–209.

A similar arrangement can be used to separate particles. Consider a mixture of particles of two different sizes suspended in water in one box and pure water in the other. If the demon opens and closes the door between the boxes quickly enough so that none of the larger particles have time to diffuse through the doorway, but long enough so that some of the smaller particles have enough time to diffuse into the other box, some separation will be achieved.

Recently two experiments have been done where a spatially asymmetric potential is periodically applied in the presence of a number of Brownian particles. Faucheux, L. S. et al. (1995), "Optical thermal ratchet," Physical Rev. Letters 74:1504–1507; Rousselet, J. et al. (1994), "Directional motion of Brownian particles induced by a periodic asymmetric potential," Nature 370:446–448.

This has been shown to lead to a directed motion of the particles at a rate depending on the diffusion coefficient. One experiment (Rousselet, J. et al. (1994), "Directional motion of Brownian particles induced by a periodic asymmetric potential," Nature 370:446–448) used microfabricated electrodes on a microscope slide to apply an electric field for the potential. This idea is also the subject of European Patent Publication 645169 of Mar. 29, 1995, for "Separation of particles in a fluid—using a saw-tooth electrode and an intermittent excitation field," Adjari, A. et al. The other experiment (Faucheux, L. S. et al. (1995), "Optical thermal ratchet," Physical Rev. Letters 74:1504–1507) used a modulated optical tweezer arrangement.

Diffusion is a process which can easily be neglected at large scales, but rapidly becomes important at the microscale. The average time for a molecule to diffuse across a distance d is $2t=d^2/D$ where D is the diffusion coefficient of the molecule. For a protein or other large molecule, diffusion is relatively slow at the macro-scale (e.g., hemoglobin with D equal to $7 \times 10^{-7}$ cm$^2$/s in water at room temperature takes about $10^6$ seconds (ten days) to diffuse across a one centimeter pipe, but about one second to diffuse across a ten micron channel).

Using tools developed by the semiconductor industry to miniaturize electronics, it is possible to fabricate intricate fluid systems with channel sizes as small as a micron. These devices can be mass-produced inexpensively and are expected to soon be in widespread use for simple analytical tests.

A process called "field-flow fractionation" (FFF) has been used to separate and analyze components of a single input stream in a system not made on the microscale, but having channels small enough to produce laminar flow. Various fields, including concentration gradients, are used to produce a force perpendicular to the direction of flow to cause separation of particles in the input stream. See, e.g., Giddings, J. C., U.S. Pat. No. 3,449,938, Jun. 17, 1969, "Method for Separating and Detecting Fluid Materials;" Giddings, J. C., U.S. Pat. No. 4,147,621, Apr. 3, 1979, "Method and Apparatus for Flow Field-Flow Fractionation;" Giddings, J. C., U.S. Pat. No. 4,214,981, Jul. 29, 1980), "Steric Field-Flow Fractionation;" Giddings, J. C., et al., U.S. Pat. No. 4,250,026, Feb. 10, 1981, "Continuous Steric FFF Device for The Size Separation of Particles;" Giddings, J. C., et al., (1983), "Outlet Stream Splitting for Sample Concentration in Field-Flow Fractionation," Separation Science and Technology 18:293–306; Giddings, J. C. (1985), "Optimized Field-Flow Fractionation System Based on Dual Stream Splitters," Anal. Chem. 57:945–947; Giddings, J. C., U.S. Pat. No. 4,830,756, May 16, 1989, "High Speed Separation of Ultra-High Molecular Weight Polymers by Hyperlayer Field-Flow Fractionation;" Giddings, J. C., U.S. Pat. No. 4,141,651, Aug. 25, 1992, "Pinched Channel Inlet System for Reduced Relaxation Effects and Stopless Flow Injection in Field-Flow Fractionation;" Giddings, J. C., U.S. Pat. No. 5,156,039 Oct. 20, 1992, "Procedure for Determining the Size and Size Distribution of Particles Using Sedimentation Field-Flow Fractionation;" Giddings, J. C., U.S. Pat. No. 5,193,688, Mar. 16, 1993, "Method and Apparatus for Hydrodynamic Relaxation and Sample Concentration in Field-Flow Fraction Using Permeable Wall Elements;" Caldwell, K. D. et al., U.S. Pat. No. 5,240,618, Aug. 31, 1993, "Electrical Field-Flow Fractionation Using Redox Couple Added to Carrier Fluid;" Giddings, J. C. (1993), "Field-Flow Fractionation: Analysis of Macromolecular, Colloidal and Particulate Materials," Science 260:1456–1465; Wada, Y., et al., U.S. Pat. No. 5,465,849, Nov. 14, 1995, "Column and Method for Separating Particles in Accordance with their Magnetic Susceptibility." None of these references disclose the use of a separate input stream to receive particles diffused from a particle-containing input stream.

A related method for particle fractionation is the "Split Flow Thin Cell" (SPLITT) process. See, e.g., Williams, P. S., et al. (1992), "Continuous SPLITT Fractionation Based on a Diffusion Mechanism," Ind. Eng. Chem. Res. 31:2172–2181; and J. C. Giddings U.S. Pat. No. 5,039,426. These publications disclose devices with channels small enough to produce laminar flow, but again only provide for one inlet stream. A further U.S. patent to J. C. Giddings, U.S. Pat. No. 4,737,268, discloses a SPLITT flow cell having two inlet streams; however the second inlet stream is not an indicator stream, but rather a particle-free stream. Giddings U.S. Pat. No. 4,894,146 also discloses a SPLITT flow cell having two input streams, but no indicator stream. All these SPLITT flow methods require the presence of more than one output stream for separating various particle fractions.

None of the foregoing publications describes a channel system device capable of analyzing small particles in very small quantities of sample which may also contain larger particles, particularly larger particles capable of affecting the indicator used for the analysis. No devices or methods using indicator streams within the cell system device are described.

Microfluidic devices allow one to take advantage of diffusion as a rapid separation mechanism, which also allows for efficient and precise detection of the separated (diffused) particles. Flow behavior in microstructures differs significantly from that in the macroscopic world. Due to extremely small inertial forces in such structures, practically all flow in microstructures is laminar. This allows the movement of different layers of fluid and particles next to each other in a channel without any mixing other than diffusion. On the other hand, due to the small lateral distances in such channels, diffusion is a powerful tool to separate molecules and small particles according to their diffusion coefficients, which is generally a function of their size. A sample stream can be in laminar flow with a stream containing an indicator substance, which provides a means for detecting an analyte which has diffused from the sample stream into the indicator stream.

Weigl, B. H. and Yager, P. "Silicon-Microfabricated Diffusion-Based Optical Chemical Sensor," Sensors & Actuators B—"Europetrode" (Conference) Apr. 2, 1996, Zurich, Switzerland; Weigl, B. H., Holl, M. A., Schutte, D., Brody, J. P., and Yager, P. "Diffusion-Based Optical Chemical Detection in Silicon Flow Structures," Analytical Methods and Instrumentation, μTAS 96 special edition, 1996; Weigl, B. H., van den Engh, G., Kaiser, R., Altendorf, E., and Yager, P. "Rapid Sequential Chemical Analysis Using Multiple Fluroescent Reporter Beads," μTAS 96, Conference Proceedings, 1996; Weigl, B. H., Hixon, G. T., Kenny, M., Zebert, D., Dwinnell, S., Buj, T. and Yager, P. "Fluorescence Analyte Sensing in Whole Blood Based on Diffusion Separation in Silicon-Microfabricated Flow Structures, SPIE Proceedings, Feb. 9–11, 1997, J. Lakowitz (ed.), Fluorescence Sensing Technology III; and Brody, J. and Yager, P. "Low Reynolds Number Micro-Fluidic Devices," Solid State Sensor and Actuator Workshop, Hilton Head, S.C. Jun. 2–6, 1996, all of which are incorporated by reference in their entirety, describe various devices and methods utilizing laminar flow and diffusion principles to detect the presence of and determine the concentration of various analytes in samples, e.g., whole blood.

U.S. patent application Ser. No. 08/625,808 "Microfabricated Diffusion-Based Chemical Sensor," filed Mar. 29, 1996 now U.S. Pat. No. 5,716,852, issued on Feb. 10, 1998, U.S. patent application Ser. No. 08/829,679 (Attorney Docket No. 6-96A) "Microfabricated Diffusion-Based Chemical Sensor," filed Mar. 31, 1997 and P.C.T. patent application Ser. No. PCT/US 97/05245 "Microfabricated Diffusion-Based Chemical Sensor," filed Mar. 31, 1997, each of which is hereby incorporated in its entirety by reference herein, disclose a microfabricated device comprising a laminar flow channel, at least two inlets in fluid connection with the laminar flow channel for conducting into the flow channel an indicator stream and a sample stream, and an outlet. Smaller particles in the sample stream diffuse into the indicator stream, forming a detection area wherein measurements of a detectable property are made. These three applications disclose methods for determining the concentration of analytes in a sample stream by detecting the position within the laminar flow channel of analyte particles from the sample stream diffusing into the indicator stream causing a detectable change in the indicator stream. Alternatively, the position within the laminar flow channel of the region where equilibrium of diffusion of the analyte from the sample stream into the indicator stream has occurred can be used to determine analyte concentration. Additionally, information useful for determining the concentration of analyte particles in the sample stream may be obtained by providing means such as specimen channels for conducting specimen streams from the indicator stream at successive intervals along the length of the laminar flow channel. Changes in the intensity of the signals from specimen channel to specimen channel may be used to calculate the concentration of analyte particles in the original sample.

The devices of these three applications can be in fluid connection with a device such as that disclosed in U.S. patent application Ser. No. 08/534,515 "Silicon Microchannel Optical Flow Cytometer," filed Sep. 27, 1995, now U.S. Pat. No. 5,726,751, issued on Mar. 10, 1998 which is incorporated in its entirety by reference herein, which allows for single-file flow of particles and which provides reflective surfaces for detection of reflected light rather than transmitted light. The devices of these three applications can alternatively be in fluid connection with a sheath flow module as disclosed in U.S. patent application Ser. No. 08/823,747 "Device and Method for 3-Dimensional Alignment of Particles in Microfabricated Flow Channels," filed Mar. 26, 1997, which is hereby incorporated in its entirety by reference herein.

The use of quality control materials and internal standard materials is, of course, well known in the art. See L. A. Kaplan, *Clinical Chemistry,* 1989, 2nd ed., The C. V. Mosby Co., St. Louis, which is incorporated by reference herein to the extent that it is not inconsistent with the disclosure herein, for a discussion of previously known methods and materials for quality control, internal standards, and calibrators. The purpose of quality control of analytical testing is to make certain that each measurement performed on a sample is reliable. In general, in previously known methods of using quality control materials, as described in Kaplan's *Clinical Chemistry,* p. 278, a control is measured daily (or once per shift) and can be plotted in a Levy-Jennings plot which graphs the established target average±two standard deviations (on the y-axis) versus time, e.g., the days of the month (on the x-axis). The target value is the estimated concentration of the analyte of interest in the sample within a certain degree of accuracy, because on any given day, the measured control value will differ slightly within the specifications of the instrument, calibration, etc. The user must establish a target value for each analyte by regular laboratory procedures known in the art. However, the measured control value should be fairly constant over time. If the control values slowly drift down or up for the target value, then this indicates a trend. If the control values show a sudden jump in the values recorded from one average to another, then this indicates a shift. If a systematic bias is indicated (a change in accuracy) or a change in precision is indicated, the user must check the reagents, internal standards, and instrumentation.

As described in Kaplan's *Clinical Chemistry,* the purpose of internal standards is to improve accuracy and precision as well as providing a check of quality control because for a given internal standard batch, its measured value (e.g., detectable property correlatable to concentration, as determined by any of various detecting means) should be the same over time.

In previously known methods and materials for quality control and using internal standards, quality control materials were different from those used for internal standards.

SUMMARY OF THE INVENTION

This invention relates generally to microsensors and methods for analyzing the presence and concentration of small particles in streams containing these small particles by diffusion principles. The invention is useful, for example, for analyzing blood to determine the concentration of small particles such as hydrogen, sodium or calcium ions in a stream containing cells, or for analyzing drinking water to determine its purity.

This invention provides a device for detecting the presence or determining the concentration of analyte particles in a sample stream comprising:

a) a laminar flow channel;
b) at least three inlet means in fluid connection with the laminar flow channel for respectively conducting into the laminar flow channel (1) at least one indicator stream, the indicator stream(s) preferably comprising an indicator substance, for example, a pH-sensitive dye, which indicates the presence of the analyte particles of interest by a detectable change in property when contacted with the analyte particles, (2) at least one sample stream, and (3) at least one reference stream, which may be used as a control stream, an internal standard stream, or both, or as a calibration stream;
c) wherein the laminar flow channel has a dimension (either depth and/or width) sufficiently small to allow laminar flow of the streams adjacent to each other and a length sufficient to allow analyte particles to diffuse into the indicator stream(s) to form a detection area;
d) outlet means for conducting the streams out of the laminar flow channel.

In the simplest embodiment of this invention, a single indicator stream, a single sample stream, and a single reference stream are used; however, the methods and devices of this invention may also use multiple sample and/or indicator and/or reference streams, all in laminar flow.

The methods of this invention are designed to be carried out in a device comprising microchannels of a size such that the Reynolds number for flow within the channel is below about 1. Reynolds number is the ratio of inertia to viscosity. Low Reynolds number means that inertia is essentially negligible, turbulence is essentially negligible, and the flow of the two adjacent streams is laminar, i.e., the streams do not mix except for the diffusion of particles as described above.

A method is provided herein for detecting the presence and/or determining the concentration of analyte particles in a sample stream, preferably a liquid stream, comprising:

a) conducting the sample stream into a laminar flow channel;
b) conducting an indicator stream, the indicator stream preferably comprising an indicator substance which indicates the presence of the analyte particles by a change in a detectable property when contacted with particles of the analyte, into the laminar flow channel, whereby the sample stream and the indicator stream flow in adjacent laminar flow in the channel;
c) conducting a reference stream, containing a constant concentration, including zero up to saturation, of reference particles, preferably analyte of the same type as those in the sample stream, which is a control stream, an internal standard stream, or a calibration stream, into the laminar flow channel, whereby the reference stream flows in a laminar stream adjacent to the indicator stream in said channel;
d) allowing analyte particles to diffuse into said indicator stream from said sample stream;
e) allowing reference particles to diffuse into said indicator stream from said reference stream; and
f) detecting the presence or determining the concentration of analyte and reference particles in the indicator stream.

The methods and devices of the present invention provide for running a control for each sample simultaneously with running the sample (not only once per day or once per 8-hour shift as in previously known methods of quality control). The control can also serve as an internal standard. The internal standards of this invention do not require an exogenous material, i.e., material different from the analyte of interest. Because a control of this invention can also serve as an internal standard, the methods and devices of this invention provide enhanced efficiency of fluid analysis over previously known methods and devices.

BRIEF DESCRIPTION OF THE DRAWINGS

FIG. 4B is a schematic representation of the flow channels of the device of FIG. 4A and the inlet channels in fluid communication therewith.

FIG. 4C is a side view of 4B.

FIGS. 7A–7C, show an embodiment of this device wherein flow rate is controlled by employing a common (shared) pumping means.

DETAILED DESCRIPTION OF THE INVENTION

Figure 1:
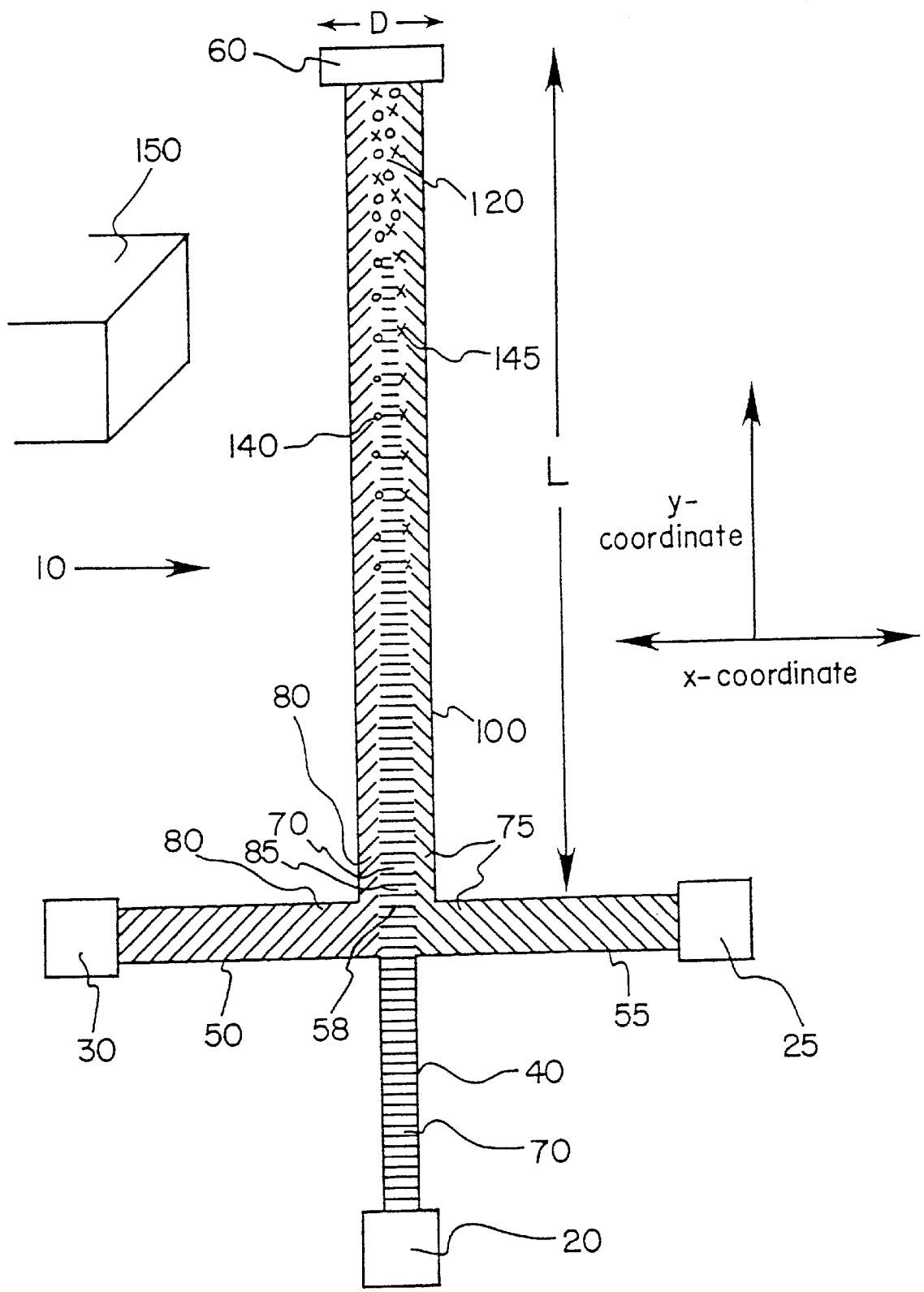
FIG. 1 is a schematic representation of flow of sample, reference and indicator streams, and the changes in indicator stream resulting from diffusion of analyte particles from sample and reference streams, in an embodiment of this invention.

This invention provides devices and methods for simultaneously monitoring one or more sample streams while monitoring one or more reference streams. The reference streams are controls streams and/or internal standard streams. These devices and methods thereby provide for determining the concentration of an analyte in a sample while continuously calibrating the device because an internal standard stream with a known concentration of the analyte of interest may be in laminar flow with the sample. These devices and methods further provide for determining the concentration of an analyte in a sample with increased accuracy as a result of including one or more internal standard streams in laminar flow with the sample: fluctuations in light source, temperature changes, variations in indicator concentration, sample turbidity and color etc. are accounted for (subtracted out). These devices also provide for continuous monitoring of the accuracy of the system as a result of using a control stream of a constant concentration.

As will be understood by those of ordinary skill in the art, generally, the more frequently a device is calibrated, the more accurate the measurements obtained thereby. The use of internal standards allows for maintaining accuracy of measurements despite less frequent calibration and/or for increasing accuracy of measurements related to the frequency of calibration.

The methods and devices of the present invention utilize diffusion of particles of interest from one laminar stream into an adjacent laminar stream. Diffusion serves not only as a means of separating smaller particles from a sample stream, but importantly also to facilitate detecting and analyzing such particles, e.g., determining the concentration of such particles, upon their diffusion from sample streams into indicator streams.

Control streams contain constant concentrations of the particles of interest, preferably close to the estimated concentrations of the particles of interest in the sample stream. Preferably the control streams also use the same carrier fluid and other components as the sample stream. Control streams are used to indicate whether or not the device and/or detection system is providing consistent results over time, or whether the device or system needs to be adjusted because the results are changing over time. Generally, results not within two standard deviations of the mean established for previous measurements of particle concentration in the control stream indicate that the device or system needs adjusting.

Internal standard streams contain constant concentrations of particles of interest which may be the same or different from the estimated concentration of said particles in the sample stream, or contain constant concentrations of another (exogenous) material. Internal standard streams are used as a basis of comparison with the sample stream so that the results from measurement of particle concentration in the sample stream may be adjusted to take into account variations in system parameters which act equally on the sample stream and the internal standard stream. The term "reference stream" encompasses both control streams and internal standard streams and in a preferred embodiment, the same stream may be used as both a control stream and an internal standard stream. When such a single reference stream is used as both a control and an internal standard stream, it will have the composition of a control stream as described above. The term "reference stream" also encompasses calibration streams as hereinafter described. The term "reference particles" refers to the particles of interest (i.e., particles to be detected and/or measured) in the reference stream.

The reference stream can be monitored concurrently with the sample stream, in the same flow channel. Detection of particles of interest upon their diffusion into indicator streams from reference streams used as control streams and internal standard streams provides for continuous quality control checks and for accounting for experimental conditions which could lead to decreased accuracy in measured values, respectively. Such experimental conditions include light source fluctuations, detector sensitivity variations, temperature fluctuations, flow rate fluctuations, indicator concentration and quality/purity, and sample turbidity. Running internal standards simultaneously with the sample allows for increased accuracy in the values measured. Use of a control stream can alert the user that the system's function has changed substantially over time since initial calibration as a result of factors such as power fluctuating warm-up of electronics or lamps, or misalignment caused by moving the instrument so that such conditions can be corrected.

The devices and methods of this invention are more convenient to the user than other devices and methods for detecting the presence or determining the concentration of analytes in a sample because this invention allows for less frequent calibration. The devices and methods of this invention eliminate the necessity for separate calibration runs by the user because the use of controls simultaneously and in the same flow channel with the sample stream provides information indicating whether the given calibration curve (which may be determined by the manufacturer and may not need to be determined by the user) is continually valid, and the use of internal standards simultaneously and in the same flow channel provides information about reaction conditions which affect the measured values for a sample and allow correction thereof.

An advantage of the devices and methods of this invention is that one fluid stream (herein referred to as a reference stream) can serve as 1) a control, 2) an internal standard, and/or 3) both a control and an internal standard. Running one or more reference streams simultaneously with the sample provides convenience and efficiency over previously known methods and devices for fluid analysis.

In the simplest embodiment (See FIG. 1) wherein a single sample stream, a single indicator stream, and a single reference stream are conducted into a device of this invention, there are two analyte detection areas: 1) a sample analyte detection area, formed by diffusion of sample analyte particles into the indicator stream and 2) a reference analyte detection area, formed by diffusion of reference analyte particles into the indicator stream. Because the reference stream can be a control stream, an internal standard stream or a calibration stream, the reference analyte detection area can be either a control analyte detection area, an internal standard analyte detection area or a calibration detection area.

The term "sample value" refers to the measured value of a detectable property exhibited by the indicator substance in the sample analyte detection area. Likewise, the term "reference value" refers to the measured value of a detectable property exhibited by the indicator substance in the reference analyte detection area. The term "internal standard value" refers to the measured value of a detectable property exhibited by the indicator substance in the internal standard analyte detection area. The term "control value" refers to the measured value of a detectable property exhibited by the indicator substance in the control analyte detection area.

Measurements of a detectable property can also be taken in regions of the sample stream, reference stream and indicator stream elsewhere than the analyte detection areas to give background, i.e., baseline, measurements of a detectable property. Many substances and solutions have low background fluorescence levels, e.g., whole blood emits a very low level of (background) fluorescence due to certain components such as low-concentration metabolites and nutrients fluorescing. The term "internal standard background value" refers to the measured value of a detectable property in the internal standard stream, i.e., not in an analyte detection area. The term "control background value" refers to the measured value of a detectable property in the control stream, i.e., not in an analyte detection area. The term "sample background value" refers to the measured value of a detectable property in the sample stream, i.e., not in an analyte detection area. The term "indicator background value" refers to the measured value of a detectable property in a region of the indicator stream where no analyte particles have diffused into it, or substantially no analyte particles have diffused into it such that no detectable property is detectable, i.e., not in an analyte detection area.

The preferred embodiments of this invention utilize liquid streams, although the methods and devices are also suitable for use with gaseous streams.

The term "detection" as used herein means determination that a particular substance is present. The methods and apparatuses of this invention can also be used to determine the concentration of a substance in a sample stream.

The term "estimated concentration" as used herein means that the concentration is known within a certain degree of accuracy. Preferably measured values of this estimated concentration should be within±two standard deviations of the estimated, target value.

The term "particles" refers to any particulate material including molecules, cells, suspended and dissolved particles, ions and atoms. The particles can be organic or inorganic.

The device of the present invention is preferably calibrated prior to measuring a given sample or plurality of samples. Calibration may also be performed during sample measurement using calibration streams.

The term "calibration stream" as used herein refers to a stream containing a known concentration, including a concentration of zero, of the analyte of interest. Calibration streams are used to determine calibration curves, which relate analyte concentrations to measured values of a detectable property of the analyte. The concentrations of a plurality of calibration streams versus their corresponding measured values of a detectable property, e.g., fluorescence or absorbance, are graphed to yield a calibration curve. Calibration streams, and the resulting calibration curves derived therefrom, provide values of a detectable property to which a sample or reference can be compared. Calibration streams can be run and measured before or after sample streams are run and measured. Preferably, a device is calibrated before its use and preferably only once. Calibration may also be performed simultaneously with running the sample by running one or more, preferably a plurality of calibration streams in the system along with the sample stream.

Calibration is performed to account for the geometrical parameters (structural variations), e.g., flow channel widths and depths, and surface reflectivity, in the device itself. A manufacturer can manufacture a large number of devices in a batch, e.g., 10,000 to 100,000 silicon chips with a device of this invention on each. The manufacturer can then calibrate a small percentage of the devices in this batch, e.g., 5–10 devices, and determine calibration curves with a certain degree of accuracy. For example, calibration may determine that the average flow channel width (the dimension orthogonal to the diffusion direction; the width is the optical path dimension for optical detection embodiments) is 50 micrometers and that it varies between 49 and 51 micrometers. Thus, a user knows that the values obtained from any device in this batch are accurate within 4% and therefore may choose not to calibrate the device.

Calibration is performed by measuring a detectable property, e.g., fluorescence, of a stream containing a known concentration of an analyte. Any section of the device which may be monitored for sample measurements may be calibrated. A calibration stream of a known concentration of a substance which has a detectable property is monitored at all sections of the flow channel where sample measurements may be taken, thereby yielding a calibration curve for that analyte. The same device can also be calibrated for any of a number of other analytes, e.g., certain proteins, pH, cations, viruses, etc.

As will be understood by those in the art, calibration streams can be general to most, or any, analytes to be analyzed, or a calibration stream can be specific to the analyte to be analyzed. For example, if the analyte is human serum albumin, the sample may be analyzed with a device calibrated with a general art-known calibration solution, e.g., rhodamine. Alternatively, the device may be calibrated with a calibration stream containing a known concentration of human serum albumin. The choice of calibration solutions/streams can be made by routine choice without undue experimentation, as those in the art recognize that the accuracy of measurements depends on calibration solutions and frequency.

A manufacturer can perform calibrations so that a user need not calibrate the device. A user then can use internal standards to account for experimental conditions which could corrupt the measured values. A user can calibrate the device, in addition to the manufacturer's previous calibration, if greater accuracy is desired.

In certain embodiments of this inventions, a manufacturer may calibrate a device for various analytes and provide the user with the same number of calibration curves, for example in a software package. In this case, the user can input the analyte being measured so the program could correctly compare the data to the correct calibration curve.

The input sample stream may be any stream containing particles, including particles of different sizes, for example blood, contaminated drinking water, contaminated organic solvents, urine, biotechnological process samples, e.g., fermentation broths and immunoassays, drug analysis samples and the like. The input sample stream is not necessarily contaminated: pure drinking water and high grade chemicals can be analyzed with the devices and methods of this invention to determine concentrations of analytes which are not contaminants, e.g., sodium ions in clean drinking water and protons in chemical solutions (to determine the pH thereof). The analyte may be any small particle in the input sample stream which is capable of diffusing into the indicator stream in the device, e.g., oxygen molecules, protons, calcium or sodium ions, proteins, e.g., albumin, organic molecules, drugs, pesticides, and other particles. In a preferred embodiment when the sample stream is whole blood, small ions such as protons and sodium ions diffuse rapidly across the channel, whereas larger particles such as large proteins, diffuse slowly. An advantage of the device and methods of this invention is that they provide for separation of small analyte particles by diffusion from larger particles, thereby facilitating detection and measurement of smaller particles by optical means. Larger particles tend to scatter light used by optical detection means, thus it is preferable to separate larger, light-scattering particles from smaller analyte particles. Preferably the analyte particles are no larger than about 3 micrometers, more preferably no larger than about 0.5 micrometers, or preferably are no larger than about 1,000,000 MW, and more preferably no larger than about 50,000 M.W.

One or more reference streams can be run and measured simultaneously with a sample stream. That is, one or more reference streams can be run and measured in the same flow channel at the same time as (and in laminar flow with) sample stream(s) and indicator stream(s). A sample stream is adjacent to an indicator stream (on a first side thereof), and an indicator stream is adjacent (on the second side thereof) to a reference stream. That is, both a sample stream and a reference stream are adjacent to an indicator stream.

Control streams provide for quality control checks on various parameters in the devices and methods of this invention, including flow rate. Quality control (QC) of the sample flow rate can be performed by plotting a QC chart (Levy-Jennings plot) of the measured control value, i.e., concentration of analyte as determined by known detection means, e.g., fluorescence, versus the sample number. Alternatively, a QC chart (Levy-Jennings plot) can be made of the position (x-coordinate) in the diffusion dimension (depth) of the peak intensity measured versus the sample number.

Alternatively, quality control of the sample flow rate can be achieved by using the same pumping means, e.g., motor, to pump the sample and reference streams in the laminar flow channel of the device. In this embodiment each of the inlet ports can be equipped with a syringe, and each syringe can be driven by one motor, to ensure consistent flow rate. A fluctuation in flow rate of the sample stream will be immediately apparent by noting a corresponding fluctuation in the control stream. Again, a QC plot (Levy-Jennings) of either the measured control stream's analyte concentration or the measured position (x-coordinate) of the control stream peak versus the sample number provides an easy means for checking control stream flow rate.

Because both the sample stream and the reference stream (s) are pumped by the same source, then the flow rate in one stream is the same as the flow rate in another stream. This assumes that no blockage of the inlet channels is present. Therefore, it may be preferable to include a flow rate sensor in each inlet channel to confirm flow rate consistency.

The term "controlling for flow rate" as used herein refers to determining that a sample stream is flowing at a given (desired) flow rate by monitoring the flow rate of a control stream.

The term "internal standard stream" as used herein refers to a stream containing a constant, estimated or known concentration of particles, preferably analyte particles, of interest. The internal standard stream preferably contains analyte particles of the same type, i.e., of the same chemical and molecular structure as the analyte particles in the sample stream. For example, if the analyte to be analyzed in the sample stream is calcium ions, then the internal standard stream contains a constant concentration of calcium ions. The term "constant" as used herein means substantially unchanging. Although an exogenous substance, i.e., a substance absent from the sample, may be used and measured as reference particles in the internal standard stream, such an exogenous material need not be included in the internal standards of this invention because the internal standard particles are not added to the sample stream as in prior art methods, but are measured in a separate stream. A detectable property, e.g., fluorescence, proportional to the concentration of the reference particle of interest, is measured in the internal standard analyte detection area in the same flow channel at the same time the detectable property is measured in the sample analyte detection area. The ratio between the latter value and the former value may be determined, sample value/internal standard value, or internal standard value/sample value, to provide or corrected value for determining sample concentration, e.g., by comparing to a calibration curve.

Using the ratio of the sample value to the internal standard value provides a method of accounting for or compensating for, i.e., correcting for, certain experimental conditions which could decrease the accuracy of the measured values, e.g., variations in light source intensity over time, variations in dye intensity (e.g., dye bleaching), variations in flow speeds between one sample run and the next. Running the internal standard in the same flow channel at the same time, i.e., in the same run, with the sample provides that the same experimental conditions are affecting both the internal standard stream(s) and the sample stream(s), and to the same degree. Accounting for these experimental conditions increases the accuracy of the measured values for the sample streams.

To further check the accuracy of the measured values of the sample streams, the ratios of the sample value to the internal standard value (preferably using the same concentration in each internal standard stream) for a plurality of samples can be graphed, yielding a line or curve of corrected values. A control stream can be run and measured, along with the same internal standard. The ratio of the control value to the internal standard value should fall on the graphed line of corrected values.

Other mathematical operations can be performed on the data collected from such a device. For example, the following ratios are useful for improving the accuracy of the sample's measured value:

(sample value–sample background value)/(reference value–reference background value);

{(sample value–sample background value)/(reference value–reference background value)}/indicator background value; and (sample value–indicator background value)/(reference value–indicator background value).

As will be understood by those of ordinary skill in the art, including more than one internal standard per sample allows for even greater correction of the measured values and various mathematical manipulations are used to make these corrections. For example, if the analyte is sodium ions, it may be preferable to use two internal standard streams: one with a high concentration of sodium ions, the other with a low concentration of sodium ions. Alternatively, if the sample stream is whole blood, it may be preferable to use two internal standard streams: one containing BC1 (which contains low concentrations of certain blood components), and the other containing BC2 (which contains high concentrations of those same blood components). Another example of using two internal standards is the case where a sample is analyzed for two analytes, e.g., calcium ions and human serum albumin (HSA). In this case, the sample stream is in the middle of the flow channel. On one side of the sample stream is an indicator stream which indicates the presence and concentration of calcium ions, on the other side of the sample stream is an indicator stream which indicates the presence and concentration of HSA. On the second side of the calcium indicator stream is an internal standard stream containing a constant, preferably known, concentration of calcium. On the second side of the indicator stream is an internal standard stream containing a constant, preferably known, concentration of HSA. Thus, there is an internal standard stream for each analyte.

In embodiments wherein two or more internal standards are used for a given sample, they must be compared to the calibration curve to determine whether the calibration curve is equally accurate for them, i.e., whether each of the internal standard values is equally close to the calibration curve. The mathematical operations to be performed on the sample values and a plurality of internal standard values depends on whether the calibration curve is equally accurate for each of the plurality of internal standards.

If the calibration curve is equally accurate for each of the plurality of internal standards, then, for example, the sample value can be divided by each of the internal standard values. Among the various mathematical operations which can be performed on data obtained from a case wherein two internal standards are run with one sample, the measured sample value can be divided by each of the two measured internal standard values. Alternatively, the two internal standard values can be averaged and then the sample value can be divided by this average. As those in the art understand, the choice of mathematical operation to be performed on the sample value with the internal standard values is dictated by the mathematical operation performed on the calibration values and internal standard values when determining the calibration curve to be used: the internal standard values are used mathematically in the same way in each case, whether in determining a calibration curve or correcting a sample measurement.

If the calibration curve is not equally accurate for each of the plurality of internal standards, as determined by plotting a plurality of internal standard values against the calibration curve for the device, then the mathematical function describing the relationship between the internal standard values can be mathematically linked, e.g., by multiplication, to the function describing the calibration curve, to yield a corrected calibration curve. In general, a calibration curve has a certain degree of accuracy only within a certain concentration range. Therefore, in some cases, for example, a high concentration internal standard value will be farther from the calibration curve than, say, a low concentration internal standard value. Hence, multiplying the function describing the relationship between these two internal standard values by the original calibration curve yields a corrected calibration curve. Upon determining a sample value, one can then relate it to an internal standard value, e.g., by dividing the sample value by the internal standard value, if the calibration values were divided by internal standard values to determine the original calibration curve. This yields a dimensionless number which can be compared to the (corrected) calibration curve to yield a concentration of analyte, i.e., the dimensionless number is found on the y-axis of the calibration curve, and the corresponding x-axis (concentration) value is read from the calibration curve.

In one embodiment, both a high and a low concentration of reference particles of interest is used for calibration and for sample correction. For example, calibration streams containing 5, 10, and 15 g/100 mL HSA are run and monitored for fluorescence. Internal standard streams containing 3 g/100 mL (low) and 18 g/100 mL (high) are simultaneously run and monitored for fluorescence. Fluorescence intensity of each of the calibration streams (containing 5, 10, and 15 g/100 mL HSA) are plotted versus fluorescence intensity of the low concentration control stream plus the fluorescence intensity of the high concentration internal standard divided by two. This yields a calibration curve to which sample values can be compared. Sample values divided by the average of internal standard values, for which the calibration curve has already been determined to be equally valid, can also be compared to such a calibration curve.

Devices of this invention may be calibrated for spatial variations in light intensity and light collection efficiency in the following way: the entire channel is flooded with a dye solution with a spectrum similar to that of the indicator (preferably the indicator itself saturated with analyte) to provide what should, under ideal circumstances, be a uniform optical image. The inverse of this image is then multiplied by all sample images used to "normalize (correct for) the response of the optical system in subsequent sample measurements with multiple streams.

If two compositionally different indicator streams are used, two reference streams, each of which contains both analytes to which the two indicators react can be used, unless one indicator is cross-sensitive to both analytes. Alternatively, if two compositionally different indicator streams are used, two reference streams, one containing only one analyte to which one of the indicator streams is sensitive and a second reference stream containing a different analyte to which the other indicator stream is sensitive, can be used.

In another embodiment, an indicator stream can include a reagent which reacts, e.g., chemically reacts, with an analyte in a sample to form a product which is detected by another indicator stream. An example of an embodiment using a plurality of indicator streams of different composition is a device having four inlet streams flowing in laminar flow wherein a middle stream is an indicator stream containing a reagent. For example, on the far left of the device is a sample stream of blood, the next stream toward the right is an indicator stream containing glucose oxidase (a reagent), the third stream is an indicator stream containing pH sensitive dye, and the fourth stream (on the far right) is a control stream containing a known amount of gluconic acid. As glucose particles from the sample stream diffuse through the reagent stream they are changed to gluconic acid which is detected by a pH-sensitive dye when the gluconic acid molecules diffuse into the indicator stream. Gluconic acid molecules from the control stream also diffuse into the indicator stream. The fluorescence from each side of the indicator stream can be measured. The fluorescence value from the side of the indicator stream nearest the sample stream (i.e., the sample analyte detection area) indicates the amount of gluconic acid derived from, and therefore the amount of glucose in, the sample, which can be compared to the value obtained for the control stream analyte detection area, which serves as a (quality control) check of the sample's measured value.

The system can also include an indicator stream introduced into one of the inlet means comprising a liquid carrier containing substrate particles such as polymers or beads having an indicator substance immobilized thereon, as disclosed in U.S. patent application "Fluorescent Reporter Beads for Fluid Analysis," Ser. No. 08/621,170, filed Mar. 20, 1996, now U.S. Pat. No. 5,747,349, issued on May 5, 1998, and incorporated in its entirety by reference herein. Such substrate particles having an indicator substance immobilized thereon are large enough (have small enough diffusion coefficients) that their diffusion out of the indicator stream is negligible at most, i.e., not substantial. The liquid carrier can be any fluid containing an indicator substance and which is capable of accepting particles diffusing from the sample and/or reference streams. Preferred indicator streams in cases where the sample is whole blood comprise water and solutions having the same osmotic pressure as whole blood such as salt water with a salt concentration of about 10 mM NaCl, KCl or MgCl, or organic solvents like acetone, isopropyl alcohol, ethanol, or any other convenient liquid which does not interfere with the effect of the analyte on the indicator substance or detection means.

If the concentration of analyte particles is high, i.e., high enough to saturate the indicator substance, then measurements can be taken at the leading edge of the analyte detection area where there is a local excess of indicator particles. The "leading edge" refers to the boundary of the analyte detection area and the indicator stream, i.e., that edge of the analyte detection area farthest from the stream from whence the analyte particles are diffusing.

Calibration streams, control streams and internal standard streams can all be streams containing a known concentration of the analyte of interest, i.e., they may be compositionally the same. They differ among each other with respect to their purpose and to when and how frequently they are used. Calibration streams are used to calibrate the devices of this invention, i.e., to account for the dimensions and specific details of the device, such as channel width. Calibration can be performed only once for a given device and is performed before, after or during the time sample measurements are taken. If greater accuracy is desired, calibration can be performed more frequently. Internal standard streams are used to account for, i.e., subtract out, effects of experimental conditions which corrupt the values measured; they are run at the same time in the same flow channel as the sample. Control streams serve as a quality control check of the measured values and preferably are run at the same time and in the same flow channel as the sample.

A given stream may serve both as a control stream and as an internal standard stream. For example, in an embodiment wherein there are three input streams—a sample stream, an indicator stream, and a reference stream containing a constant, estimated concentration of the analyte of interest— the measured value of a detectable property, e.g., fluorescence intensity, can be measured in the reference analyte detection area. This value can be compared against what is known to be a reasonable value, based on a calibration curve. In this sense, the reference stream is serving as a quality control check, i.e., a control stream. Additionally, the (same) measured value of a detectable property can serve as an internal standard, e.g., the sample value can be divided by the internal standard (reference) value to correct for experimental conditions. Hence, one reference stream can yield data (a measured detectable value) which can serve as both a control and an internal standard. Of course, it is preferable to have both an internal standard stream and a control steam, so that the control stream can be corrected by mathematical manipulation using the measured value of the internal standard stream.

The term "laminar flow channel" as used herein means a channel which allows for laminar flow under hydrodynamic conditions, defined by viscosity and flow speed. For a channel of given dimensions, laminar flow can be achieved for a liquid of certain viscosity and flow speed. The dimensions of the device are chosen such that laminar flow is maintained, i.e., low Reynold's number, preferably below about 1. That is, at least one dimension—either the depth and/or the width—is small enough to maintain a low Reynold's number and hence laminar flow. The laminar flow channel is long enough to permit small analyte particles to diffuse from a sample stream, and from a reference stream if such reference stream contains analyte particles, and have a detectable effect on an indicator substance or detection means, preferably at least about 2 mm long. In preferred embodiments of this invention, the channel length (L) (see FIG. 1) is between about 5 mm and about 50 mm. The channel depth (d)(diffusion direction) is preferably between about 20 micrometers and about 1 mm. The channel is more preferably made relatively deep, e.g., at least about 200 micrometers, which makes it easier to measure indicator fluorescence with simple optics, and less likely for particles to clog the channel. However, the channel can be made as shallow as possible while avoiding clogging the channel with the particles being used. The channel width (the dimension orthogonal to the depth and length) is small enough to allow laminar flow of two streams therein, preferably no greater than about one millimeter and more preferably between about 100 micrometers and about 400 micrometers. If the sample includes human whole blood, which contains blood cells as large as about 20–30 micrometers, preferably the depth at the T-joint is 50 micrometers.

For a given flow speed, the laminar flow channel can be made long enough to allow the indicator, reference, and sample streams to reach equilibrium with respect to the analyte particles within the channel. Equilibrium occurs when the maximum amount of smaller particles have diffused into the indicator stream from the sample stream, calibration stream and/or reference stream. Alternatively, for a given length of flow channel, the flow speed can be decreased to provide time for equilibrium to be reached. Minimum and maximum flow speeds can be determined by routine experimentation by those of ordinary skill in the art. For example, the settling rate of cells must be considered when determining the minimum flow speed for biological fluids containing cells, e.g., whole blood. Additionally, shear rates must be considered as they are the speed at which cells are moving slowly enough that their interaction with the channel walls can become greater than the force the fluid applies to the cells to keep them flowing down the flow channel. Furthermore, in cases where two or more fluids with different viscosities and velocities are in adjacent laminar flow, lysing of cells is a possibility resulting from an abrupt change in flow speeds (velocities). It may be preferable to avoid abrupt changes in flow speeds in adjacent laminar flow of fluids, for example in cases wherein the flow rate is so high that shearing forces are great enough to affect or damage analytes or other particles, e.g., lysing of cells, in the sample which would lead to interference with measurements.

The device of a preferred embodiment of this invention (see FIG. 1) comprises channel grooves in the form of a "†" or "ψ" having a central trunk and three branches etched into the surface of a silicon microchip, which surface is thereafter covered with a glass sheet. The central groove is formed of the trunk of the "†" or "ψ", and the branches are the inlet means in fluid connection with the laminar flow channel for respectively conducting the sample, reference, and indicator streams into the laminar flow channel.

Devices of this invention may also include more than three inlet branches in fluid connection with the laminar flow channel for conducting a plurality of inlet streams into said channel. These may be arranged in a "candelabra"-like array or may be arranged successively along a "crossbar" for the "†" or the branches of the "ψ" configuration, the only constraint being that laminar flow of all the streams must be preserved.

Inlet means include the inlet channels or "branches" and may also include other means such as tubes, syringes, and the like which provide means for injecting fluids into the device. Outlet means include collection ports, and/or means for removing fluid from the outlet, including receptacles for the fluid, means inducing flow by capillary action, pressure, gravity, positive displacement (e.g., pumping by syringe pumping), electroosmotic (electrokinetic) pumping and other means known to the art. Such receptacles may be part of an analytical or detection device.

Devices of this invention can comprise external detecting means for measuring a detectable property or a change in a detectable property. Detection and analysis are done by any means known to the art, including optical means, such as optical spectroscopy. Other means such as absorption spectroscopy, particularly visible but also ultraviolet and infrared; fluorescence; by chemical indicators which change color or other properties when exposed to the analyte; chemiluminescence, which is known by those in the art to refer to luminescence due to chemical reaction—all light measured is that emitted, no light is introduced into the system, and examples of chemiluminescent reagents include "lucigenin" which emits luminescence at certain (high) pH, luminol, and luciferins. Other detection means include immunological means; electrical means, e.g., electrodes inserted into the device; electrochemical means; radioactive means; or virtually any microanalytical technique known to the art including magnetic resonance techniques; or other means known to the art to detect the presence of an analyte such as an ion, molecule, polymer, virus, DNA sequence, antigen, microorganism or other factor. Preferably optical or fluorescent means are used, and antibodies, DNA sequences and the like are attached to fluorescent markers. Changes in an indicator substance carried within the indicator stream as a result of contact with analyte particles are detected, as well as background (baseline) measurements, e.g., background absorbance of the indicator stream or of the sample stream.

Preferably the detection means allows for spatial resolution, i.e., allows for locating the position at which a detectable property is measured. One can monitor the entire depth (diffusion direction) of the flow channel to identify the positions of each analyte detection area. For example, a linear diode array detector provides optical intensity (detectable property) as a function of position in the diffusion direction (channel depth). Alternatively, a charge coupled device (CCD) camera allows the user to select a magnification range such that the entire depth (diffusion direction) of the flow channel, including the edges, can be monitored.

The detecting means can be stationary, while the device of this invention (comprising the flow channel) is mobile, and measurements are taken as the device is moved, preferably automatically, with respect to the detecting means. Alternatively, the detecting means is mobile, the device is stationary, and measurements are taken as the detecting means moves with respect to the device.

As discussed above, the methods of this invention include conducting sample and reference streams in laminar flow in a flow channel with an indicator stream and detecting the presence and/or concentration of analyte and reference particles in the indicator stream. The methods may also include:

measuring a detectable property in a sample analyte detection area, thereby obtaining a sample value;

measuring the detectable property in a reference analyte detection area, thereby obtaining a reference value;

when the reference stream is an internal standard stream, correcting for experimental conditions by determining the ratio between the sample value and the reference value, and when the reference stream is a control stream, determining the constancy of the reference particle value over time.

The method can alternatively, or in addition, include any of the following steps:

when the reference stream is an internal standard stream, measuring the detectable property in the internal standard stream, thereby obtaining an internal standard background value;

when the reference stream is a control stream, measuring the detectable property in the control stream, thereby obtaining a control background value;

measuring the detectable property in the sample stream, thereby obtaining a sample background value;

measuring the detectable property in the indicator stream in a region of the indicator stream where substantially no analyte particles have diffused into it, thereby obtaining an indicator background value;

correcting for experimental conditions (improving the accuracy of the sample's measured value of analyte) by performing mathematical operations chosen from among the following:

i) subtracting the sample background value from the sample value, and then dividing this value by the reference value minus the reference background value;

ii) dividing the quotient from step i) by the indicator background value; or iii) subtracting the indicator background value from the sample value, and then dividing this value by the reference value minus the indicator background value.

As will be readily apparent to those of skill in the art, variations on the mathematical operations performed on the values determined by devices and methods of this invention are possible and fall within the scope and spirit of this application.

The flow speed of the input streams (streams introduced into the device) is preferably between about 0.05 and about 50 mm/sec. Without wishing to be bound to any particular theory, we believe that in some cases it may be preferable for the sample and indicator streams to be flowing at different rates. For example, in cases of low test sensitivity wherein the sample contains a very low concentration of analyte and/or the detectable property is inherently small, e.g., a low fluorescence quantum yield, if the indicator stream is flowing more slowly than the sample stream, then the indicator substance in the indicator stream is effectively surrounded by a greater number of analyte particles for a longer period of time, i.e., each indicator substance molecule "sees" more analyte particles because the latter move past the former more slowly. So, in these cases is it preferable to have sample and reference streams pumped by same motor and the indicator stream pumped by different motor.

The methods and devices of this invention allow for determining the viscosity of a sample stream by detecting the position within the laminar flow channel of analyte particles from the sample stream diffusing into the indicator stream causing a detectable change in the indicator stream or in an indicator substance in the indicator stream. As will be understood by those in the art, the viscosity of fluids can be changed, e.g., by addition of high molecular weight polymers such as high molecular weight dextrans. Changing the viscosity of fluids changes the velocity at which they flow under a given pressure.

The method of one embodiment of this invention includes the use of an indicator substance which is immobilized on a particulate substrate, carried within the indicator stream, as described above. The particulate substance is large enough that its diffusion out of the indicator stream is negligible, i.e., it causes no detectable change in the property being measured. The indicator substance is preferably a substance which changes in fluorescence or color in the presence of analyte particles, such as a dye, enzymes, and other organic molecules that change properties as a function of analyte concentration. The term "indicator substance" is also used to refer to polymeric beads, antibodies or the like having dyes or other indicators immobilized thereon. It is not necessary that the indicator stream comprise an indicator substance when detection means such as those directly detecting electrical, chemical or other changes in the indicator stream caused by the analyte particles are used.

Advantages of this system include the fact that analytes in turbid and strongly colored solutions such as blood, can be determined optically without the need for prior filtering or centrifugation. Cross-sensitivities of indicator dyes to larger sample components (a common problem) can be avoided because the larger particles do not diffuse into the indicator stream in the time during which the streams are in contact, and thus do not interfere with detection of the analyte. Alternatively, such cross-sensitivities can be accounted for by reference streams (internal standards). Another advantage of the device and method of this invention is that because of the small depths (diffusion direction) of the flow channels, the analyte particles travel very short distances before measurement can be made, thereby allowing measurements to be made in little time.

The indicator can be kept in a solution in which it displays its optimal characteristics (e.g., cross-sensitivities to pH or ionic strength can be suppressed by using strongly buffered solutions). In addition, the flow channel can be deep, which makes it easy to measure the indicator fluorescence with simple optics. No membrane(s) separating sample and indicator and reference streams are needed; the system is less subject to biofouling and clogging than membrane systems. The system is also tunable in that sample, reference or indicator stream concentrations and/or flow rates can be varied to optimize the signal being detected. For example, if a reaction between an analyte in a sample or reference stream and a reagent in an indicator stream yields a detectable property after about five seconds, the system can be adjusted so that the reaction product will be detected in the central portion of the device.

The method can be conducted by a continuous flow-through of sample, reference and indicator streams. The steady-state nature of this method makes longer signal integration times possible.

Devices of this invention may be fabricated by microfabrication methods known to the art, e.g., as exemplified herein, a method comprising forming channels in a silicon microchip, such as by etching grooves into the surface of the silicon microchip and placing an optically transparent, e.g., glass, cover over the surface (Brody, J. P. and Yager, P. "Low Reynolds Number Micro-Fluidic Devices" Solid State Sensor and Actuator Workshop, Hilton Head, S.C. Jun. 2–6, 1996). Precision injection molded plastics may also be used for fabrication. A lid, preferably of an optically clear material such as glass or a silicone rubber sheet, is sealed onto the etched substrate. Other means for manufacturing the devices of this invention include using silicon structures or other materials as a template for molding or micromachining the device in plastic, and other techniques known to the art. Precision injection molded plastics to form the devices can also be used. Microfabrication techniques are known to the art, and more particularly described below.

The devices of this invention are preferably microfabricated devices. The term "microfabricated" refers to devices capable of being fabricated on silicon wafers readily available to those practicing the art of silicon microfabrication and having the features, sizes and geometries producible by such methods as LIGA, thermoplastic micropattern transfer, resin based microcasting, micromolding in capillaries (MIMIC), wet isotropic and anisotropic etching, laser assisted chemical etching (LACE), and reactive ion etching (RIE), or other techniques known within the art of microfabrication. In the case of silicon microfabrication, larger wafers will accommodate a plurality of the devices of this invention in a plurality of configurations. A few standard wafer sizes are 3", 4", 6", and 8". Application of the principles presented herein using new and emerging microfabrication methods is within the scope and intent of the claims hereof.

The devices of this invention and the channels therein can be sized as determined by the size of the particles desired to be detected. As is known in the art, the diffusion coefficient for the analyte particles is inversely related to the size of the particle and thus is substantially linearly related to the size of the particle. Once the diffusion coefficient for the particles desired to be detected is known, the contact time of the two streams, size of the central flow channel, relative volumes of the streams, pressure and velocities of the streams can be adjusted to achieve the desired diffusion pattern.

Fluid dynamic behavior is directly related to the Reynolds number of the flow. In microfabricated devices, if the velocity decreases as the channel length (where the device is assumed to work in a fixed time at all scales), then the Reynolds number varies in proportion to the square of the length.

The Reynolds number is the ratio of inertial forces to viscous forces. As the Reynolds number is reduced, flow patterns depend more on viscous effects and less on inertial effects. Below a certain Reynolds number, e.g., about 1 (based on lumen size for a system of channels with bends and lumen size changes), inertial effects can essentially be ignored. The microfabricated devices of this invention do not require inertial effects to perform their tasks, and therefore have no inherent limit on their miniaturization due to Reynolds number effects. Applicants' device designs, while significantly different from previous reported designs, operate in this range. These microfabricated devices of this invention require laminar, non-turbulent flow and are designed according to the foregoing principles to produce flows having low Reynolds numbers.

The devices of the preferred embodiment of this invention are capable of analyzing a sample of a size between about 0.01 microliters and about 20 microliters within a few seconds, e.g., within about three seconds. They also may be reused. Clogging is minimized and reversible. A channel with the dimensions 400 $\mu$m (depth) by 50 $\mu$m (width), with fluids flowing at a velocity of 100 nL/s, for example, indicate a Reynolds number ($R_e$=plv/$\eta$) of 0.2 so that the fluid is in a regime where viscosity dominates over inertia.

By adjusting the configuration of the channels in accordance with the principles discussed above to provide an appropriate channel length, flow velocity and contact time between the sample, reference, and/or calibration streams and the indicator streams, the size of the particles remaining in the sample stream and diffusing into the indicator stream can be controlled. The contact time required can be calculated as a function of the diffusion coefficient of the particle D and the distance d over which the particle must diffuse by $2t=d^2/D$. Particles or molecules that have diffusion coefficients larger than D will diffuse into the indicator stream, and particles or molecules having a diffusion coefficient substantially smaller than D will not. If the diffusion coefficient of the larger particles is about ten times smaller than D, the indicator stream should be entirely free of the large particles.

In some embodiments of this invention, channels of this invention have hydrophilic surfaces to facilitate flow of liquid therein and allow operation of the device without the necessity for pressurization. The substrate may be treated to enhance surface-wetting properties by means known to the art following fabrication of the channels, to render it hydrophilic. The lid is may also be treated to render it hydrophilic.

Means for applying pressure to the flow of the fluid streams through the device may be provided at the inlets ports and/or the outlet (e.g., as vacuum exerted by chemical or mechanical means). Means for applying such pressure are known to the art, for example as described in Shoji, S. and Esashi, M. (1994), "Microflow devices and systems," J. Micromechanics and Microengineering, 4:157–171, and include the use of a column of water or other means of applying water pressure, electroendoosmotic forces, optical forces, gravitational forces, and surface tension forces. Pressures from about $10^{-6}$ psi to about 10 psi may be used, depending on the requirements of the system. Preferably about $10^{-3}$ psi is used. Most preferred pressures are between about 2 mm and about 100 mm of water pressure.

The magnitude of the pressure drop needed to obtain an average velocity, v, of a fluid with absolute viscosity, θ, and density, p, through a circular channel (length, l, diameter, d) can be calculated from Poiseuille's Law (Batchelor, G. K., *An Introduction to Fluid Dynamics*, Cambridge Univ. Press 1967), $$\frac{P}{l} = \frac{32\eta v}{d^2}$$

Using v=100 μm/sec and d=100 μm, we get a pressure drop equivalent to about 0.3 mm of H$_2$O per cm of channel length. Poiseuille's equation is only strictly valid for circular flow channels. The channels of this invention can have cross-sections of various shapes, e.g., wedge-shaped and substantially rectangular, in addition to circular. Thus, in embodiments with non-circular cross-sections, Poiseuille's equation can be considered only as an approximate relation between the variables represented.

When a liquid is introduced into a device there is at first an effective pressure, $P_{\textit{eff}}=P_0+P_{st}$, equal to the sum of the applied pressure, $P_0$, and a pressure due to the surface tension, $$P_{st} = \frac{\gamma \cos\Theta}{r}.$$

$P_{st}$ is a function of the surface tension of the fluid, γ, the contact angle of the fluid with the surface, θ, and the radius of curvature of the fluid surface, r.

For hydrophilic surfaces, cos θ is close to 1, and for small channels no applied pressure is needed to wet the device. This is referred to as "wetting by capillary action." However, once the device is completely wet, one has to consider the surface tension at the exit area. In the device described in the example hereof, the radius of curvature of the fluid in the exit area was several millimeters, so that the pressure due to the surface tension was negligible.

With a channel depth of 100 μm, $P_{st}$ is about 1 cm of H$_2$O, so surface tension on the exit port is significant. However, using an etchant such as EPW F-Etch as described below, which attacks the {100} planes of silicon, means that the corners as etched are not as sharp as shown in the figures. This results in a gradual widening of the channel to about 1 mm which reduces the effect of the surface tension.

As shown in FIG. 1, a device of this invention, in the form of a "✝" is provided, referred to herein as reference T-sensor 10. The device can be microfabricated, for example, by etching on a silicon microchip or by micromachining plastic. The geometry need not necessarily be a "✝," or a "ψ." Any angles between the channels that can be fabricated will also suffice so long as laminar flow is maintained. As discussed above, there may be a plurality of input channels. In this embodiment, it is necessary only that all input channels merge into a single flow channel, and all channels be sufficiently small that laminar flow (Reynolds number less than about 1) is maintained for all operating conditions. The sample containing small particles of interest, sample stream 80, is brought into the device through sample stream inlet port 30, from whence it flows into sample stream inlet channel 50. An indicator stream 70 is brought into indicator stream inlet port 20, from whence it flows into indicator stream inlet channel 40. A reference stream 75 is brought into reference stream inlet port 25. Detecting means 150 is positioned relative to the flow channel, e.g., above or below the channel, so that it can detect a detectable property, e.g., fluorescence or absorbance.

Sample stream 80, reference stream 75, and indicator stream 70 meet at conjunction-joint 58 at the beginning of flow channel 100, and the three streams flow in parallel, adjacent laminar flow to exit port 60 at the end of flow channel 100. The indicator stream 70 contains an indicator substance such as a dye which reacts with analyte particles in the sample stream 80 and reference stream 75 producing a detectable change in physical properties. Indicator stream 70 is shown by horizontal shading, whereas sample stream 80 and reference stream 75 are shown by diagonal shading in opposing directions in FIG. 1. Due to the low Reynolds number in the small flow channel 100, no turbulence-induced mixing occurs and the three streams flow parallel to each other without mixing. However, diffusion does act perpendicular to the flow direction, that is, perpendicular to the length (y-coordinate) so analyte particles in the sample stream and reference stream diffuse to the right and left, respectively, into indicator stream 70 and may eventually become uniformly distributed across the width of flow channel 100 at uniform analyte particle diffusion area 120.

Indicator stream 70 flows into flow channel 100 to form an initial reference area 85 into which analyte particles have not yet diffused. Analyte particles from sample stream 80 diffusing into indicator stream 70 form a sample analyte detection area 140 where analyte particles create a detectable change in indicator stream 70, preferably by causing a detectable change in property in an indicator substance within the indicator stream 70. Analyte particles from reference stream 75 diffusing into indicator stream 70 form a reference analyte detection area 145 where analyte particles create a detectable change in indicator stream 70. Particles of an indicator substance, e.g., dye particles, may also diffuse into sample stream 80 to form a diffused indicator area 110 (not shown). If this change in local concentration of the indicator substance is a problem in some applications, its diffusion rate can be made arbitrarily small by immobilization on particulate substances, e.g., polymers and reporter beads. Polymers such as high molecular weight dextrans can be used to immobilize indicator substances, thereby decreasing the diffusion coefficient of the indicator substance. The molecular weight of the polymer is preferably about 1,000 to about 100,000 g/mol. Immobilizing an indicator substance on a polymer such as a high molecular weight dextran also increases the viscosity of the indicator stream. High molecular weight polymers are generally less likely to adhere to the channel walls than are beads, which are also used to immobilize indicator substances.

In the reference T-sensor 10 of FIG. 1, a sample stream 80, e.g., blood, a reference stream 75 and an indicator stream 70 containing an indicator dye are joined at the intersection of sample stream inlet channel 50, reference stream inlet channel 55 and indicator stream inlet channel 40, with flow channel 100 (i.e., conjunction-joint 58) and flow laminarly next to each other in flow channel 100 until they exit the structure at exit port 60. Small ions such as $H^+$ and $Na^+$ diffuse rapidly across the diameter of flow channel 100, whereas larger ions such as a dye anion diffuse only slowly. Larger particles such as sugars, proteins, and the like show no significant diffusion within the time the indicator stream 70, reference stream 75 and sample stream 80 are in contact with each other. The smaller sample components diffuse more rapidly and would equilibrate closer to conjunction-joint 58 than do larger components, which would equilibrate farther up in flow channel 100 in embodiments with flow channels long enough or flow rates slow enough to allow their equilibration. As diffusion proceeds up the channel, sample analyte detection area 140 and reference analyte detection area 145 are formed.

The analyte detection areas 140 and 145 can be as large as necessary to provide a detectable indicator signal. Similarly reference area 85 can be made to be as large as necessary to provide a detectable reference background value. Adjustments of these areas will be made as described herein based on the diffusion coefficients of the analyte and indicator substance, flow rates and channel sizes.

The presence or concentration of an analyte of interest in a sample stream can be determined by comparing the sample stream's measured value (sample value) of a detectable property, e.g., visible absorbance at a certain wavelength, to the measured value of a calibration stream, a control stream or an internal standard stream (reference value). By monitoring the reference stream simultaneously with and in the same flow channel as the sample stream, the reference stream and sample stream are subject to the same experimental conditions, including those conditions which could lead to decreased accuracy in the sample's measured value, for instance a fluctuation in light source intensity. Both the sample stream and the reference stream are exposed to the same conditions; therefore, the effects of these interfering conditions are corrected for (subtracted out).

Figure 2:
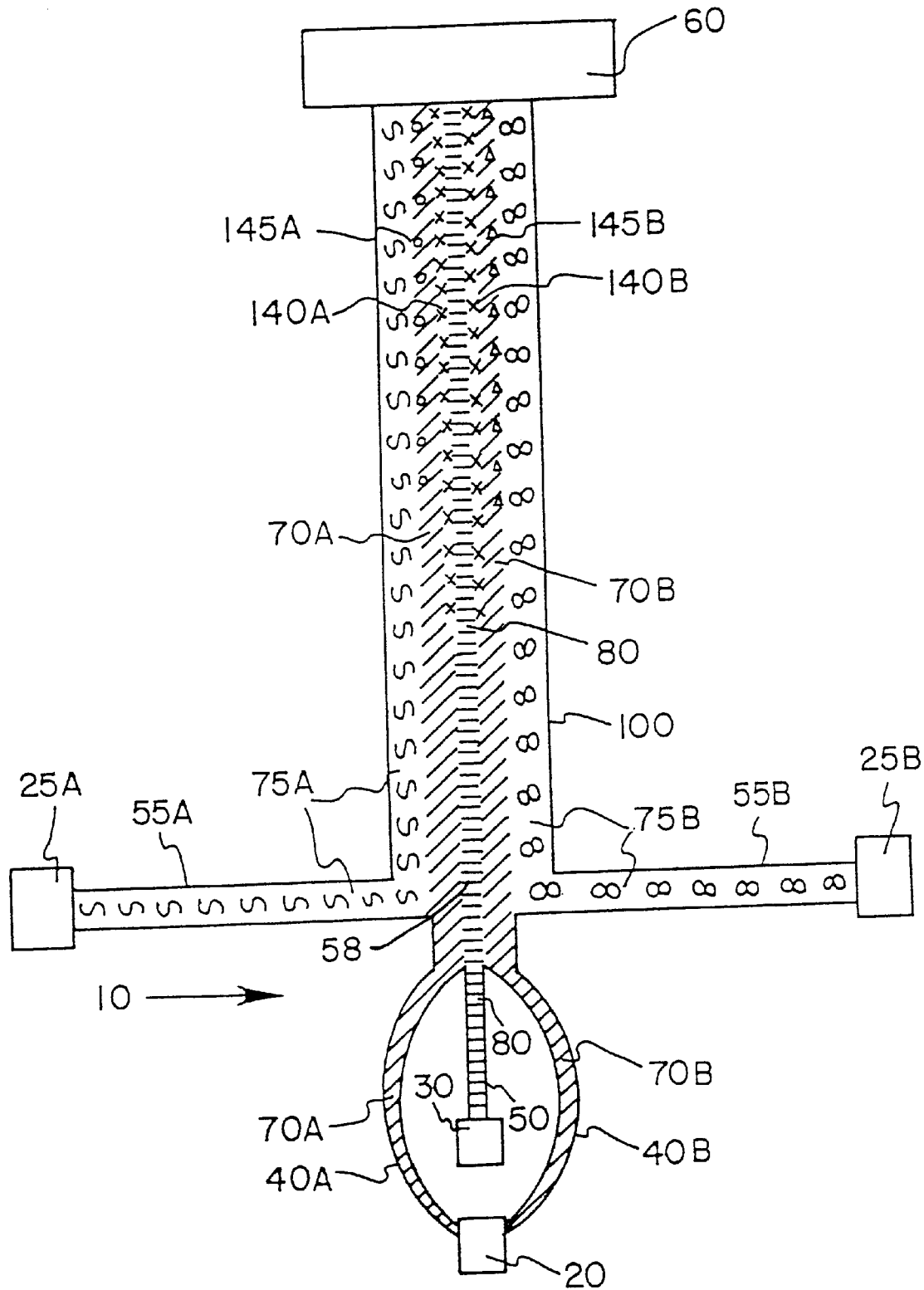
FIG. 2 is a schematic representation of flow of a sample stream, two indicator streams and two reference streams, and the changes in indicator streams resulting from diffusion of analyte particles from sample and reference streams, in another embodiment of this invention. In this embodiment the two indicator streams are in fluid connection with a single indicator stream inlet port.

FIG. 2 shows a device of this invention wherein two indicator streams 70A and 70B flow into flow channel 100 from a common (shared) indicator stream inlet port 20, thereby leading to two laminar flows of (the same) indicator stream 70A and 70B, both adjacent to sample stream 80. Indicator streams 70A and 70B and sample stream 80 are shown by diagonal and horizontal shading, respectively, whereas reference streams 75A and 75B are shown by wavy lines (like sideways "S") and sideways "8," respectively, in FIG. 2. Sample stream 80 contains small molecules of interest, and is brought into the device through sample stream inlet port 30, from whence it flows into sample stream inlet channel 50. Indicator stream 70A and 70B are brought into indicator stream inlet port 20, from whence they flow into indicator stream inlet channels 40A and 40B. Two reference streams 75A and 75B are brought into reference stream inlet ports 25A and 25B, respectively. Reference streams 75A and 75B may be of the same or of different composition, e.g., one may contain a high concentration of the analyte of interest and the other may contain a low concentration of the analyte of interest. A detector (not shown in FIG. 2) is positioned relative to the flow channel, e.g., above or below the channel, so that it can detect a detectable property, e.g., fluorescence or absorbance.

Sample stream 80, reference streams 75A and 75B, and indicator streams 70A and 70B meet at conjunction-joint 58 at the beginning of flow channel 100, and the five streams flow in parallel laminar flow to exit port 60. Analyte particles in the sample stream 80 and reference streams 75A and 75B diffuse into indicator streams 70A and 70B. Analyte particles in sample stream 80 diffuse left and right (perpendicular to the direction of flow) into indicator streams 70A and 70B to form sample analyte detection areas 140A and 140B (shown in FIG. 2 by "X"). Analyte particles in reference stream 75A diffuse right (perpendicular to the direction of flow) into indicator stream 70A to form reference analyte detection area 145A (shown in FIG. 2 by circles). Analyte particles in reference stream 75B diffuse left (perpendicular to the direction of flow) into indicator stream 70B to form reference analyte detection area 145B (shown in FIG. 2 by triangles). By adjusting flow rate and flow channel length, equilibration of diffusion can be accomplished.

The device in FIG. 2 provides for two reference streams to be in laminar flow with the sample stream. For example, one reference stream can be an internal standard stream, which contains a known or "estimated" concentration of the analyte of interest. The measured value of a detectable property for the sample (sample value), or preferably plurality of samples, is divided by the measured value of a detectable property for an internal standard (internal standard value). The internal standard functions to correct for (subtract out) experimental conditions which would otherwise decrease the accuracy of the measured values. The other reference stream can be a control stream, which also contains a known or estimated concentration of the analyte of interest, and is otherwise identical to the sample. The control serves as a (quality control) check of the determined concentration of the analyte in the sample. Both the measured value of a detectable property for the sample (sample value) and for the control (control value) are divided by the measured value of a detectable property for the internal standard (internal standard value). The determined concentration of the analyte in the sample, obtained from the measured value of a detectable property for the sample (sample value), should agree with the measured value of a detectable property for the control, i.e., they should both have minimal and similar deviation from the calibration curve. As will be apparent to those in the art, if more than one internal standard is used, more complicated mathematical operations can be performed on the data obtained by the device and method of this invention to improve the accuracy of the determined concentration of analyte in a sample.

Figure 3:
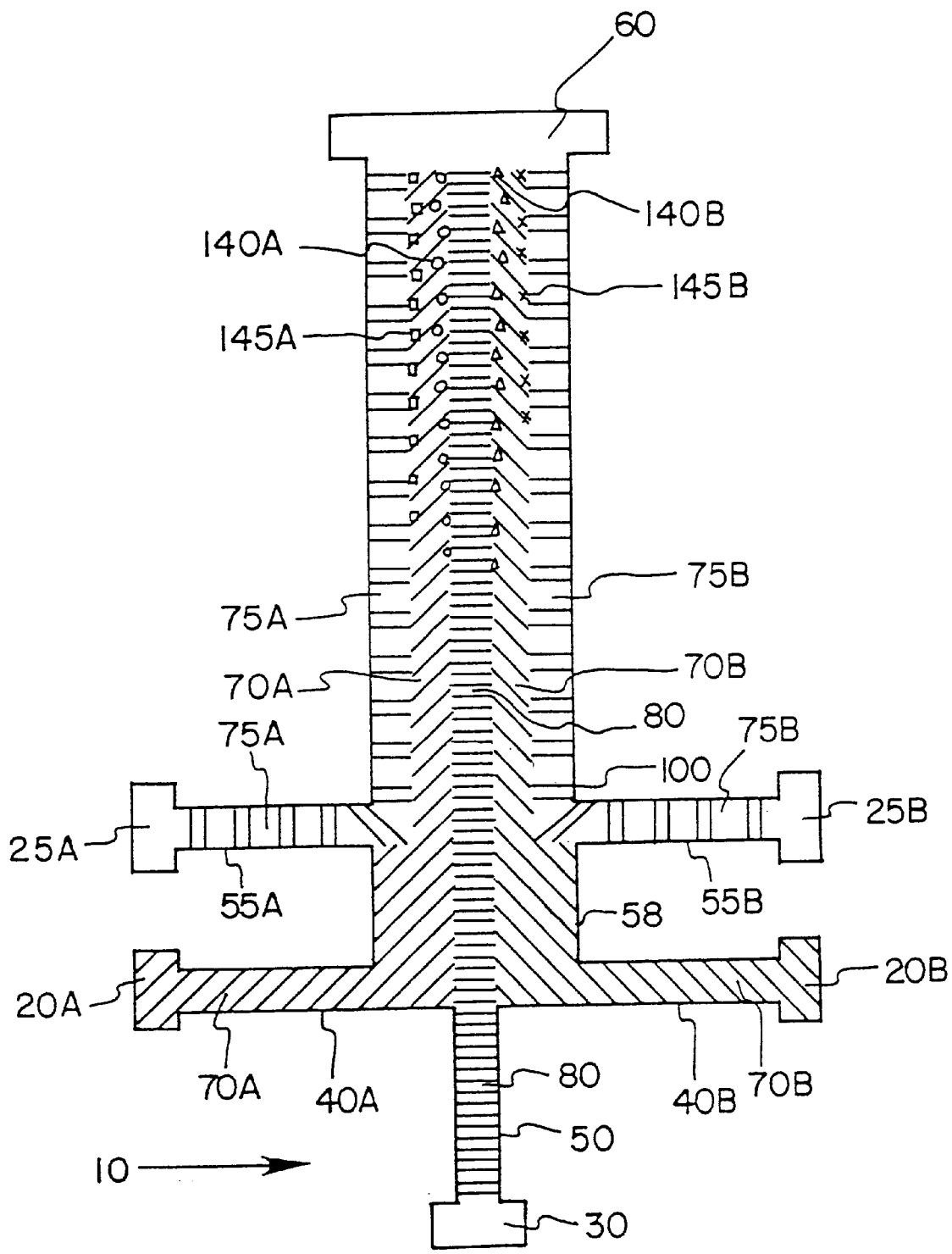
FIG. 3 is a schematic representation of flow of a sample stream, two indicator streams and two reference streams, and the changes in indicator streams resulting from diffusion of analyte particles from sample and reference streams, in another embodiment of this invention. In this embodiment each of the two indicator streams has a separate inlet port.

FIG. 3 shows another embodiment of the device of this invention wherein two indicator streams 70A and 70B flow in laminar flow adjacent to sample stream 80. Indicator streams 70A and 70B are shown by diagonal shading, whereas reference streams 75A and 75B and sample stream 80 are shown by horizontal shading, unevenly and evenly spaced, respectively. Sample stream 80 contains small particles of interest, and is brought into the device through sample stream inlet port 30, from whence it flows into sample stream inlet channel 50 and then into flow channel 100. Indicator streams 70A and 70B are brought into indicator stream inlet ports 20A and 20B, respectively, from whence they flow into indicator stream inlet channels 40A and 40B, respectively, and then into flow channel 100. Two reference streams 75A and 75B (of the same composition in this example) are brought into reference stream inlet ports 25A and 25B, respectively. From reference stream inlet ports 25A and 25B, the two reference streams 75A and 75B flow into reference stream inlet channels 55A and 55B and then into flow channel 100. A detector (not shown in FIG. 3) is positioned relative to the flow channel so that it can detect a detectable property.

Sample stream 80, reference streams 75A and 75B, and indicator streams 70A and 70B meet at conjunction-joint 58 in flow channel 100, and the five streams flow in parallel laminar flow to exit port 60. Analyte particles in the sample stream 80 and reference streams 75A and 75B diffuse into indicator streams 70A and 70B. Analyte particles in sample stream 80 diffuse left and right into indicator streams 70A and 70B, respectively, to form sample analyte detection areas 140A and 140B (shown in FIG. 3 by circles and triangles, respectively). Analyte particles in reference streams 75A and 75B diffuse right and left, respectively, into indicator streams 70A and 70B to form reference analyte detection areas 145A and 145B (shown in FIG. 3 by squares and "x's," respectively). In this embodiment, as in the one in FIG. 2, by adjusting flow rate and flow channel size, equilibration of diffusion can be accomplished.

The device in FIG. 3 provides for two indicator streams to be in laminar flow with the sample stream and reference streams. For example, one indicator stream can be an indicator for one analyte of interest, e.g., human serum albumin, while the other indicator stream can be an indicator for another analyte of interest, e.g., sodium ions. Reference streams, e.g., control streams containing BC1 and BC3 (which are commercially available controls for whole blood containing known concentrations of various blood components but absent red and white blood cells, and obtained from Biorad in Hercules, Calif.), may be in adjacent laminar flow with the indicator streams.

Figure 4A:
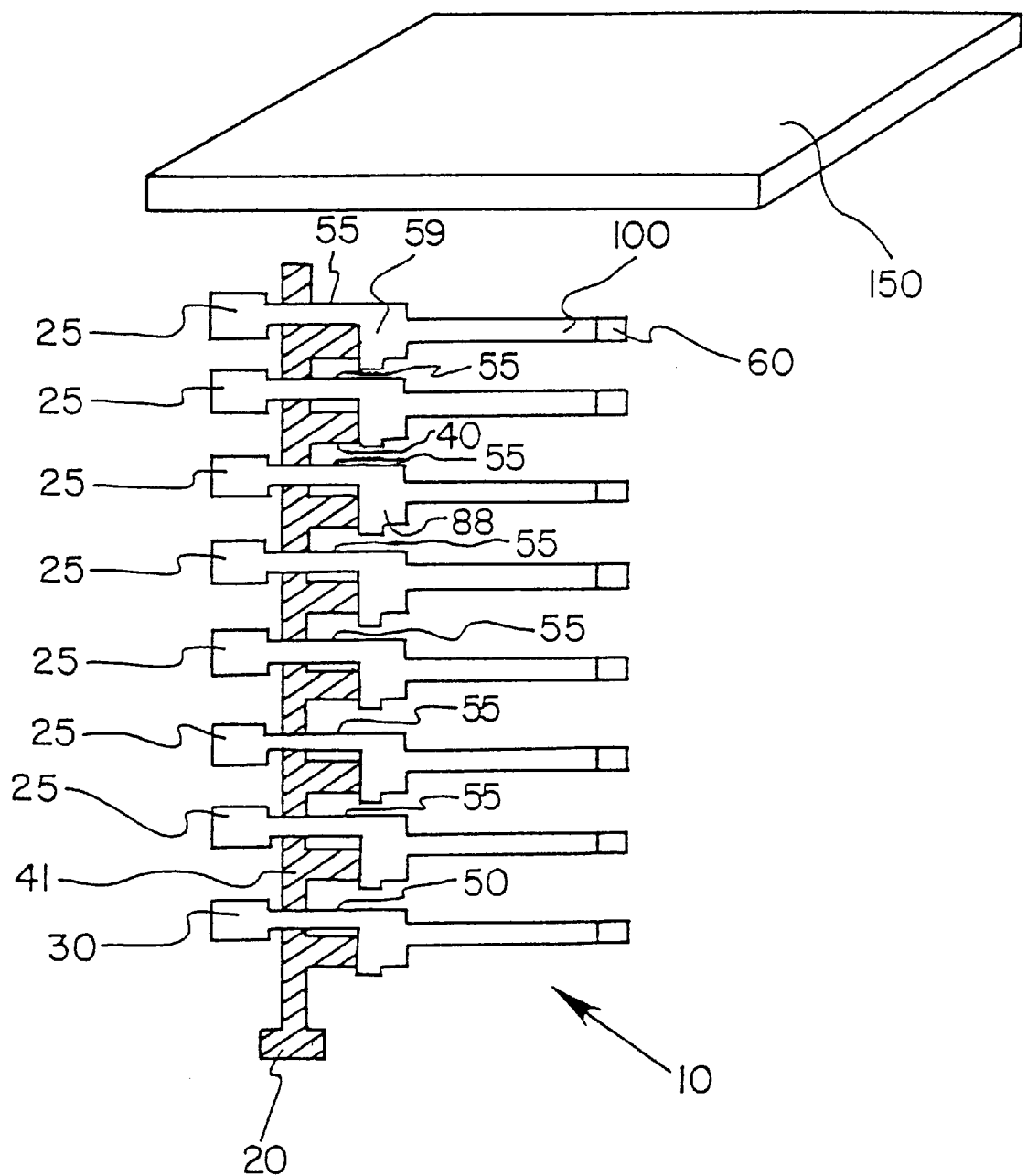
FIG. 4A is a schematic representation of another embodiment of this invention wherein a plurality of flow channels are connected in parallel via a channel on the backside of the substrate, e.g., silicon wafer.

FIG. 4A shows an embodiment of this invention wherein a plurality of T-sensor devices are in fluid connection with one another via manifold line 41. FIG. 4 shows a device with eight flow channels 100, into each of which flows 1) an indicator stream and 2) either a reference stream (in seven of the eight flow channels) or a sample (in one of the eight flow channels). In FIG. 4 flow channels 100, reference stream inlet channels 55, and sample stream inlet channel 50 are unshaded, and are all in one plane of the substrate, e.g., if the substrate is silicon, the wafer is etched to the same depth for all of these elements. Indicator stream inlet port 20, manifold line 41, and indicator stream inlet channels 40 are shaded (diagonal shading) and are in the same plane as each other but one which is different from the first plane containing the flow channels. This embodiment can be fabricated by etching flow channels 100, reference stream inlet channels 55, and sample stream inlet channel 50 from one side/face of the substrate, e.g., silicon wafer and the indicator stream inlet port 20, manifold line 41, and indicator stream inlet channels 40 from the other side/face of the substrate (silicon wafer). Through holes 88 connect the channels (100, 55 and 50) etched on one side of the substrate to the channels (40 and 41) etched on the other side of the substrate. The connection is specifically via T-joints 59 with indicator stream inlet channel 40. A transparent cover is sealed to both sides/faces of the substrate. Holes are formed in the transparent covers to provide access to the ports or the covers are positioned so that they do not cover the ports. One or more detectors are positioned relative to the flow channels so that changes in a detectable property in each flow channel can be detected and monitored.

In this embodiment a plurality (e.g., seven) of reference streams are brought into reference stream inlet ports 25, from whence the streams flow into reference stream inlet channels 55, and then into flow channel 100. The sample stream is brought into sample stream inlet port 30, from whence the sample stream flows into sample stream inlet channel 50, and then into flow channel 100. Each flow channel 100 contains an indicator stream in laminar flow with either a reference or sample stream. The streams exit through exit ports 60. In this embodiment, each flow channel 100 is connected to an indicator stream inlet channel 40 and either a reference inlet channel 55 or sample stream inlet channel 50 via a T-joint 59. Each indicator stream inlet channel 40 is connected to a manifold line 41, allowing one indicator stream inlet port 20 to feed a plurality of indicator streams into a plurality of flow channels 100.

FIG. 4B is shows a section of the device in FIG. 4A, i.e., it shows the sample stream inlet port 30, sample stream inlet channel 50, flow channel 100, in fluid connection with them, and exit port 60 all etched in one plane from one side of a silicon wafer. Also shown (by dotted lines indicating the plane behind the former plane, and thus etched from the other side of the wafer) are indicator stream inlet port 20 and indicator stream inlet channel 40. The sample stream inlet channel 50 is connected with the indicator stream inlet channel to via T-joint 59 which comprises hole 88. Eight such sections are connected in parallel fashion in the device in FIG. 4A.

FIG. 4C is a side view of FIG. 4B (FIG. 4C shows what the device of FIG. 4B rotated by 90 degrees on an axis along flow channel 100). Sample stream inlet port 30 (which extends through a first side of the wafer substrate) and sample stream inlet channel 50 (heavier lines) are closer to viewer. Flow channel 100 and indicator stream inlet channel 40 are in one plane, and connected to sample stream inlet channel 50 via through hole 88. Indicator stream inlet port 20 (dotted line) extends to the other side of the wafer.

The embodiment shown in FIG. 4A provides for simultaneous multiple referencing while running and monitoring a sample stream. It is convenient because indicator need be introduced into only one indicator stream inlet port 20. One detecting means can be used to monitor all eight flow channels 100. If greater magnification is desired, then it may be preferable to employ more than one detector. Alternatively, the device can be moved in a continuous fashion such that one detector can be used to monitor many flow channels at high magnification. However, because each reference and sample stream is in a different flow channel, some experimental conditions, e.g., differences in flow rates, cannot be accounted for (subtracted out). In this embodiment it is preferable to monitor the flow speed in each flow channel, to assure that no clogging or blockage has occurred in one flow channel, which could lead to undesired flow speeds in the other channels.

The embodiment illustrated in FIG. 4 has the advantages of using the same light source, electronics, and fluids (e.g., indicator solution). Variations in any of these can lead to decreased accuracy of measurements. Further, the multiple separate inlets allow for more accurate and independent control of flow speeds of the various fluid streams.

Figure 5:
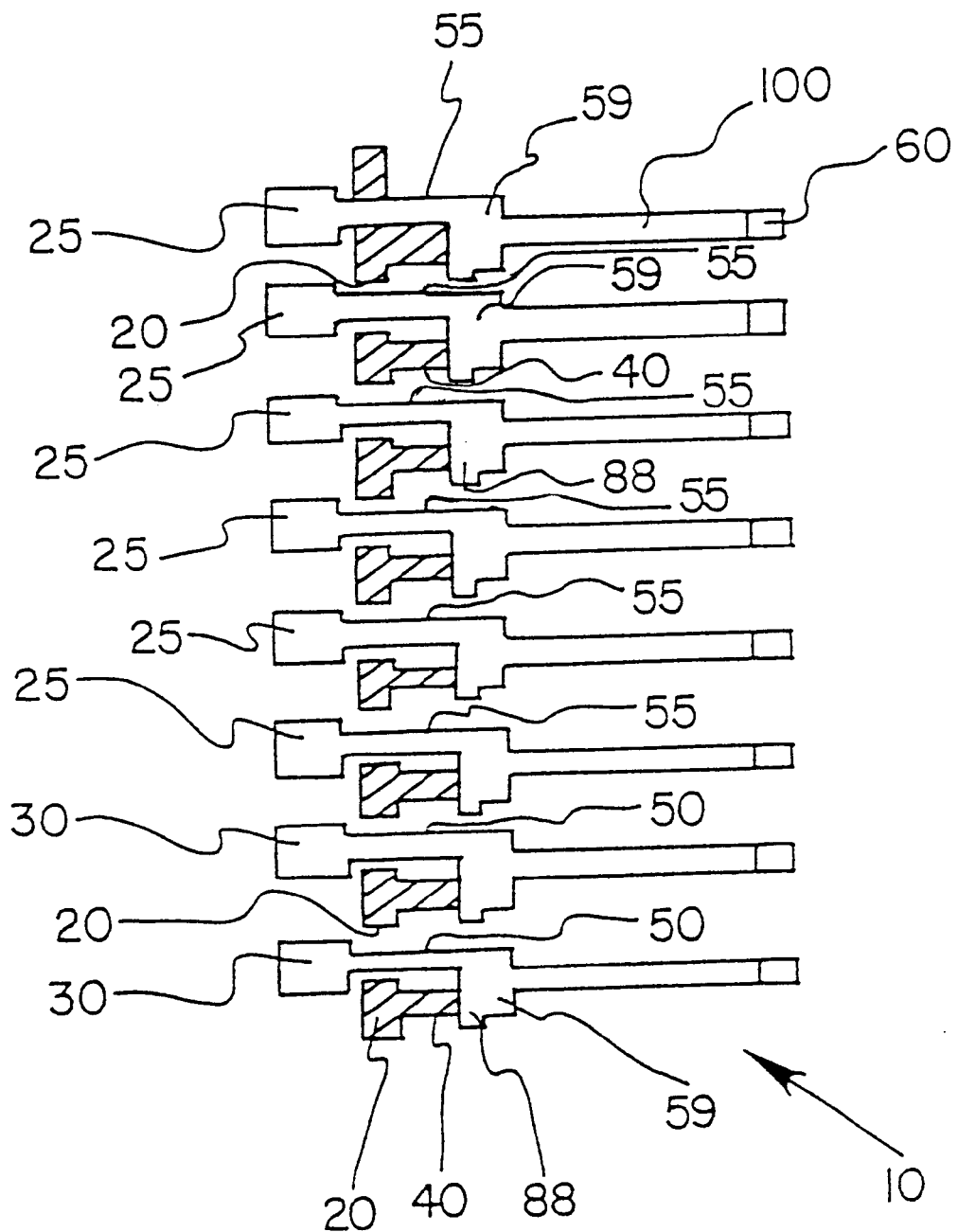
FIG. 5 is a schematic representation of an embodiment with multiple flow channels in one substrate.

FIG. 5 shows an embodiment of the device of this invention, similar to that in FIG. 4 except that there is no manifold line connecting the indicator stream inlet channels. FIG. 5 shows a device with eight flow channels 100, into each of which flows 1) an indicator stream and 2) either a reference stream (in six of the eight flow channels) or a sample (in two of the eight flow channels). In FIG. 5 flow channels 100, reference stream inlet channels 55, and sample stream inlet channels 50 are unshaded, and are all in one plane of the substrate, e.g., if the substrate is silicon, the wafer is etched to the same depth for all of these elements. Indicator stream inlet port 20 and indicator stream inlet channels 40 are shaded (diagonal shading) and are in the same plane as each other but one which is different from the first plane containing the flow channels, etc. Like the embodiment in FIG. 4, this embodiment can be fabricated by etching flow channels 100, reference stream inlet channels 55, and sample stream inlet channels 50 from one side/face of the substrate, e.g., silicon wafer and the indicator stream inlet ports 20 and indicator stream inlet channels 40 from the other side/face of the substrate (silicon wafer). A transparent cover is sealed to both sides/faces of the substrate. Holes are formed in the transparent covers to provide access to the ports or the covers are positioned so that they do not cover the ports. Like the embodiment shown in FIG. 4, the embodiment shown in FIG. 5 allows for monitoring of a plurality of flow channels with one detector (not shown in FIG. 5).

In this embodiment a plurality (e.g., six) of reference streams are brought into reference stream inlet ports 25, from whence the streams flow into reference stream inlet channels 55, and then into flow channel 100. Sample streams are brought into sample stream inlet ports 30, from whence the sample streams flow into sample stream inlet channels 50, and then into flow channel 100. Each flow channel 100 contains an indicator stream in laminar flow with either a reference or sample stream. The streams exit through exit ports 60. In this embodiment, each flow channel 100 is connected to an indicator stream inlet channel 40 and either a reference or sample stream inlet channel (55 and 50, respectively) via a T-joint 59 and a hole 88.

Figure 6:
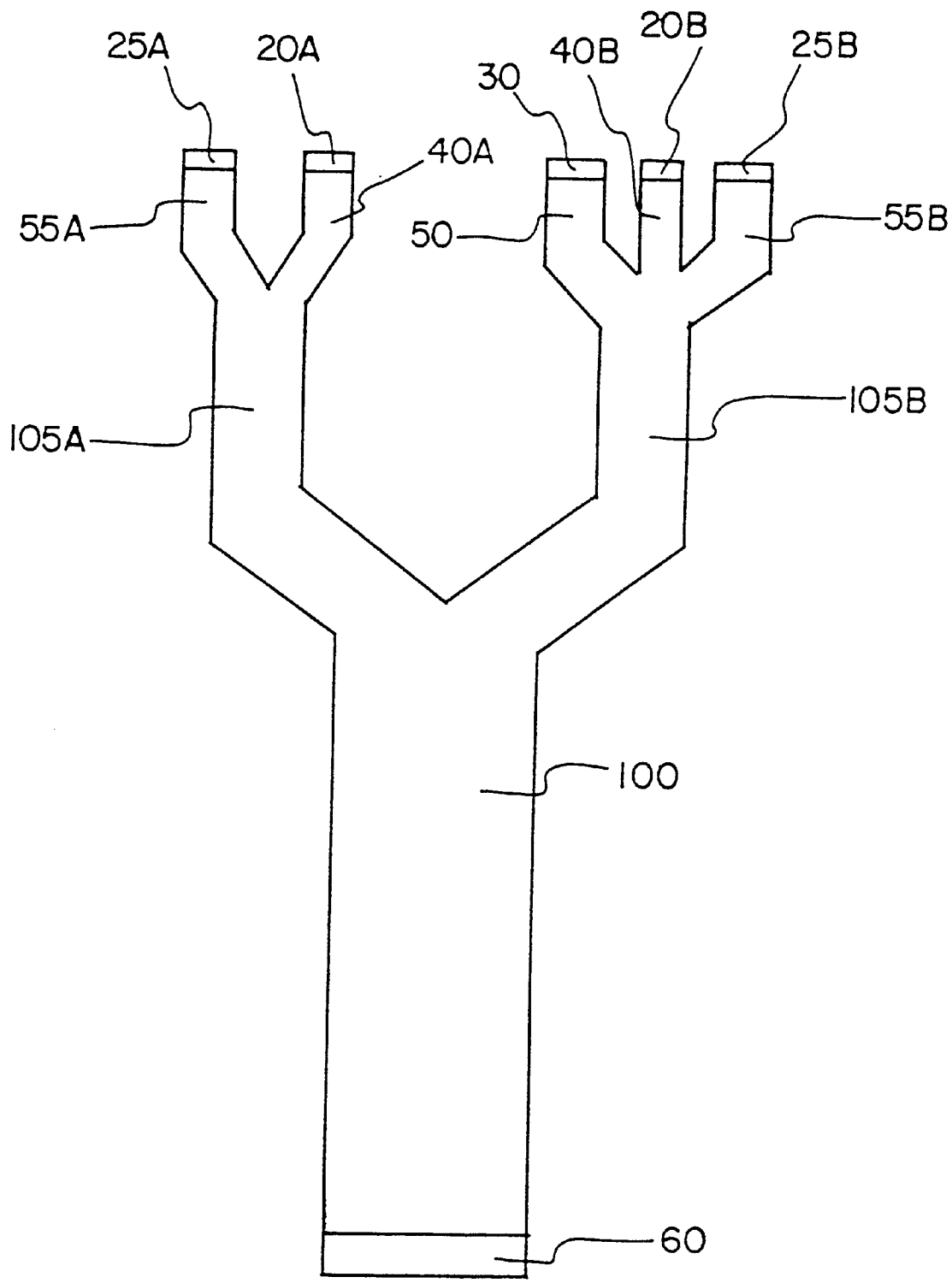
FIG. 6 shows a schematic representation of another embodiment of this device.

FIG. 6 shows other embodiments of this invention, wherein streams are introduced into ports as described and shown above, but which contain contributory flow channels 105A and 105B, which connect the inlet channels to the flow channel 100.

In the embodiment shown in FIG. 6 reference streams 75A and 75B are brought into reference stream inlet ports 25A and 25B, from whence the streams flow into reference stream inlet channels 55A and 55B, then into contributory flow channels 105A and 105B, and then into flow channel 100. A sample stream is brought into sample stream inlet port 30, from whence the sample stream flows into sample stream inlet channel 50, then into contributory flow channel 105B and then into flow channel 100. Indicator streams are brought into indicator stream inlet ports 20A and 20B, from whence the streams flow into indicator stream inlet channels 40A and 40B, then into contributory flow channels 105A and 105B, and then into flow channel 100. The streams are in laminar flow from the inlet ports to the exit port 60. The contributory flow channels 105A and 105B need not be angled as shown but may be straight or angled at a different angle so long as laminar flow is preserved.

Changes in a detectable property can be monitored in both contributory flow channels 105A and 105B and flow channel 100 by detecting devices.

Quality control of flow rate can be performed by 1) plotting a QC chart (see Example 4 below) and/or 2) using a common, i.e., shared pumping means to pump both the reference stream and the sample stream. The indicator stream can also be pumped by the common pumping means in some embodiments.

Figure 7:
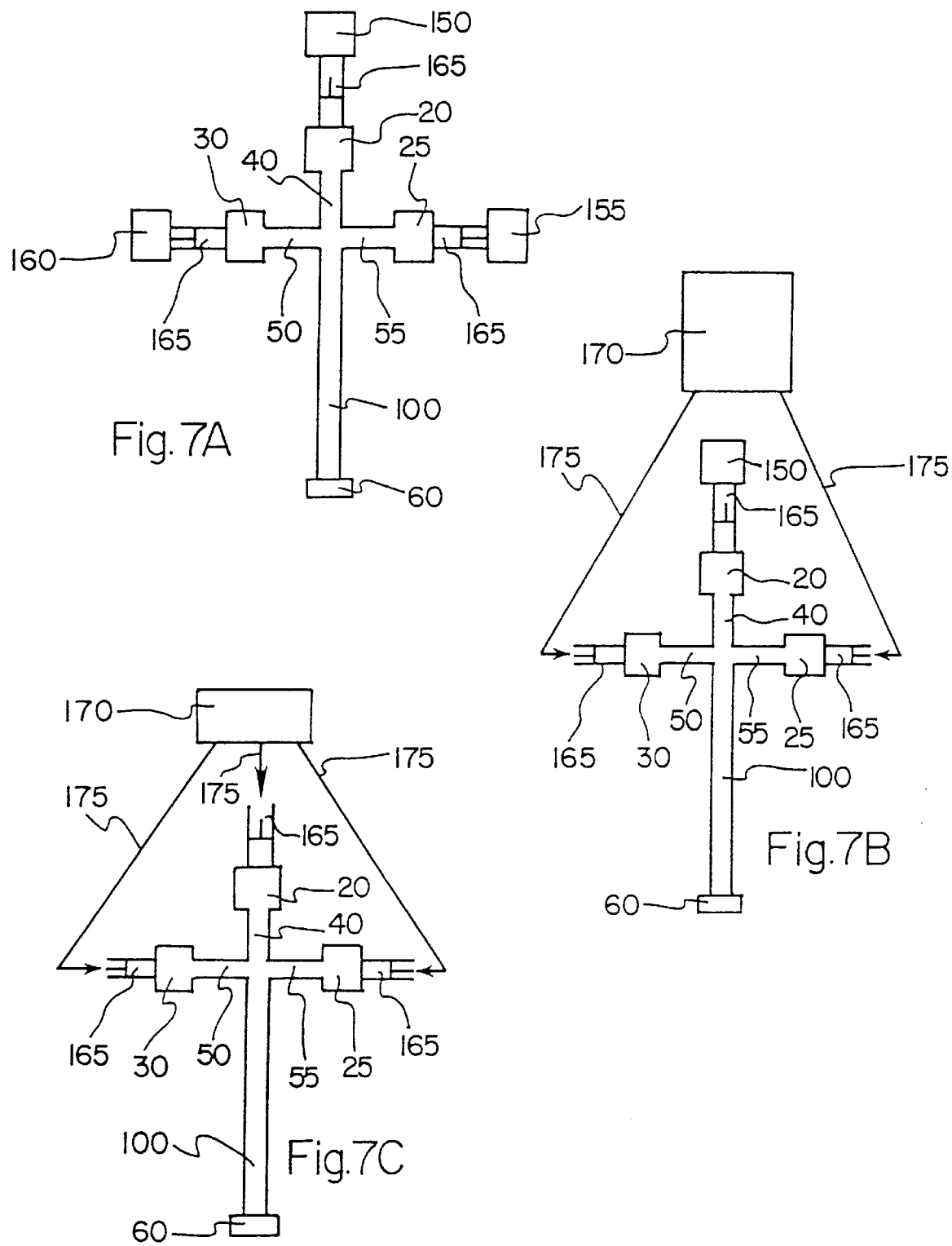
FIG. 7, comprising
Figure 8:
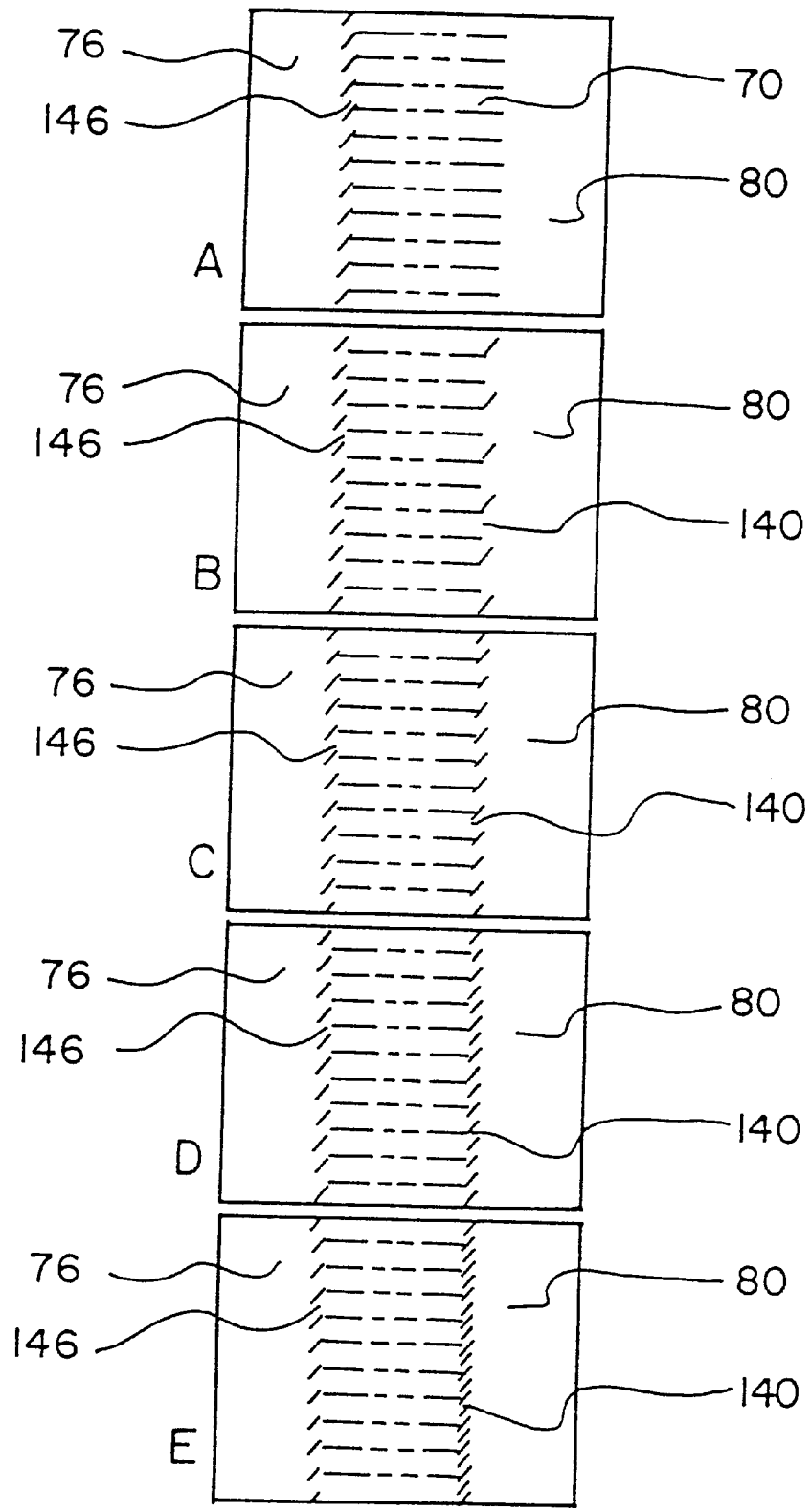
FIG. 8 is a schematic representation of five photo micrographs taken during use of the device of this invention as shown in FIG. 1.

FIG. 7A illustrates an embodiment of the device wherein separate pumping means are used for each input stream. Pumping means 150 pumps an indicator stream into and down flow channel 100 through syringe 165, indicator stream inlet port 20, and indicator stream inlet channel 40. Pumping means 155 pumps reference stream 75 into and down flow channel 100 through syringe 165, reference stream inlet port 25, and reference stream inlet channel 55. Pumping means 160 pumps sample stream into and down flow channel 100 through syringe 165, sample stream inlet port 30 and sample stream inlet channel 50.

FIG. 7B illustrates an alternative embodiment of the device wherein a shared pumping means is used for sample and reference streams. Shared pumping means 170 pumps a reference stream and sample stream into and down flow channel 100. Pumping means 150 pumps an indicator stream into and down flow channel 100.

FIG. 7C illustrates an alternative embodiment of the device wherein a shared pumping means is used for sample, indicator and reference streams. Shared pumping means 170 pumps a reference stream, indicator stream and sample stream into and down flow channel 100.

The use of a shared pumping means, e.g., a motor, assures that each stream pumped by such means is subject to the same pressure.

It may be preferable to monitor the flow rate in each inlet channel to make certain that no impediment to flow has developed, e.g., clogging, and that all streams are flowing at the desired flow rate(s).

Numerous embodiments besides those mentioned herein will be readily apparent to those skilled in the art and fall within the range and scope of this invention. All references cited in this specification, and all references cited in such references, are incorporated in their entirety by reference herein to the extent not inconsistent herewith. The following examples illustrate the invention, but are in no way intended to limit the invention.

EXAMPLES

Example 1

Fabrication of Reference T-Sensor

A two-mask level process was used to fabricate a reference T-sensor device of this invention on a silicon wafer. The reference T-sensor device had a flow channel 400 micrometers deep and 20 mm long. Three inlet channels were formed as grooves 30 mm long and 200 micrometers deep. Inlet channel and flow channel width was 50 micrometers.

The first mask level defined the inlets and exit ports, which were etched completely through the wafer to the rear side of the silicon. The second level defined the fluid transport channels, i.e., the inlet channels and flow channels.

Four inch chrome masks were made to these specifications by Photo Sciences, Inc. (Torrance, Calif.) and 3" wafers ({100}, n-type) with 500 nm of $SiO_2$ grown on them were used.

Wafers were cleaned in a Piranha bath ($H_2SO_4$ and $H_2O_2$) (2:1) before processing. A primer (HMDS spun on at 3000 rpm) was used to enhance photoresist adhesion. About one $\mu$m of AZ-1370-SF (Hoechst) photoresist was deposited by spin coating (3000 rpm), and this was followed by a soft bake (30 min at 90° C.).

A contact aligner was used to align and expose wafers. Exposure time was varied to yield best results. No post-exposure bake was done. Wafers were developed in AZ-351 (diluted 4:1) (Hoechst) for one minute and rinsed in DI water. Blue tack tape (Semiconductor Equipment Corporation, Moorpark, Calif.) was applied to the backsides of the wafers to protect the oxide from the oxide etch.

The wafers were immersed in a buffered oxide etch (BOE, 10:1 HF (49%) and $NH_4F$ (10%)) for eleven minutes to completely etch away the unprotected oxide. The blue tack tape was removed by hand, and the photoresist was removed in an acetone rinse.

Silicon etching was done in a mixture of ethylenediamine, pyro-catechol, and water (EPW F-etch as described in Reisman, A., et al. (1979) J. Electrochem. Soc. 126:1406–1415) set up in a reflux boiling flask. This etch attacks the {100} planes of silicon at a rate of about 100 $\mu$m an hour. Fluid attachment ports were etched in the first step for about three hours. Photoresist was again applied, and the mask containing flow channels between fluid ports and the barrier region was exposed. The wafers were developed and etched in this second step for about one hour.

After final processing, the wafers were once again cleaned in a Piranha bath and rinsed in DI water. They were then diced into individual devices about 1 cm by 1 cm.

Anodic bonding according to Wallis, G. and Pomerantz, D. I (1969) J. Appl. Physics 40:3946–3949, was used to attach Pyrex glass to the silicon devices. One inch square pieces of Pyrex glass (100 $\mu$m thickness) from Esco Products Inc. (Oak Ridge, N.J.) were used. First, the silicon and Pyrex glass were immersed in a solution of $H_2O_2$, $NH_4OH$, and $H_2O$ (1:4:6) heated to 50° C. This process removes any organic matter on the surfaces and also makes the surfaces hydrophilic. After 20 minutes in this solution, the silicon and Pyrex were rinsed with DI water and dried. Anodic bonding was done at 400° C. with 400 V applied between the glass and the silicon.

Example 2

Detecting and Measuring the Concentration of Human Serum Albumin in a Reference T-Sensor Five 0.1 M AMPSO (Aldrich) aqueous buffer solutions (pH 7.4), with 0, 2, 4, 6, and 8 g/100 mL of human serum albumin (HSA) were prepared from analytical grade chemicals (Aldrich). The resulting solutions were used consecutively as sample streams. The analyte in question in this experiment was HSA. A saturated solution of fluorescent albumin indicator dye AB580 (Molecular Probes, Eugene, Oreg.), was diluted by a factor of 10 with the same 0.1 M AMPSO buffer solution, and used as an indicator stream. BC1, a commercially available plasma containing 3.8 g/100 mL HSA, was used as a control stream. A flow speed of 50 nL/sec was used.

The reference T-sensor device (FIG. 1) was attached to the stage of a microscope so that the flow channel, from the T-joint up to about 500 $\mu$m from the T-joint, was in the view field of the objective. The inlet ports and the outlet port were connected to injector loops and to upright tubes which were filled with water so that there was a pressure difference of 30 mm water column between the inlet ports and the outlet port. The inlet ports were exposed to identical pressure so that the three streams joined in the middle of the T-joint, and were flowing parallel to the outlet port. One injector loop was filled with BC1 control solution, a second loop was filled indicator dye solution, and a third loop was filled with one of the sample solutions. The loops contained enough volume to operate the device for roughly one hour.

After all three injection loops were allowed to flow into the reference T-sensor device, and after 1 min of equilibration and flushing time, photographs were taken through a camera attachment on the microscope. The excitation filter center wavelength was 590 nm, and the emission filter was a longpass 607 nm filter.

The experiment yielded photographs in which the fluorescence of the analyte detection area between the indicator stream and the sample stream, and between the indicator stream and the control stream was a function of the concentration of analyte (HSA) having diffused into the indicator stream from the sample stream and control stream, respectively.

As represented schematically in FIG. 8A–8E, in each of the five cases, the photograph of the device showed the control stream 76 (shown in the Figure as white) as dark (black), the sample stream 80 (shown in the Figure as white) as dark (black), the indicator stream 70 (shown in the Figure by horizontal lines) as reddish black and the control analyte detection area 146 (shown in the Figure by diagonal hatching) as a bright red line extending along the length of the flow channel where HSA from the control stream had diffused into the indicator stream, and the sample analyte detection area 140 as a bright red line extending along the length of the flow channel where HSA from the sample stream had diffused into the indicator stream. Additionally, in the first case where the concentration of HSA in the sample stream was 0 g/100 mL buffer (FIG. 8A, Experiment A), there was no detectable analyte detection area between the indicator stream 70 and the sample stream 80. In the second case where the concentration of HSA in the sample stream 80 was 2 g/100 mL buffer (FIG. 8B, Experiment B), a sample analyte detection area 140 about half the intensity of the control analyte detection area 146 was seen. In the third case where the concentration of HSA in the sample stream 80 was 4 g/100 mL buffer (FIG. 8C, Experiment C), a sample analyte detection area 140 about the same intensity as the control analyte detection area 146 was seen. In the fourth case where the concentration of HSA in the sample stream 80 was 6 g/100 mL buffer (FIG. 8D, Experiment D), a sample analyte detection area 140 about one and a half times the intensity of the control analyte detection area 146 was seen. In the fifth case where the concentration of HSA in the sample stream 80 was 8 g/100 mL buffer (FIG. 8E, Experiment E), a sample analyte detection area 140 about twice the intensity of the control analyte detection area 146 was seen.

Figure 9:
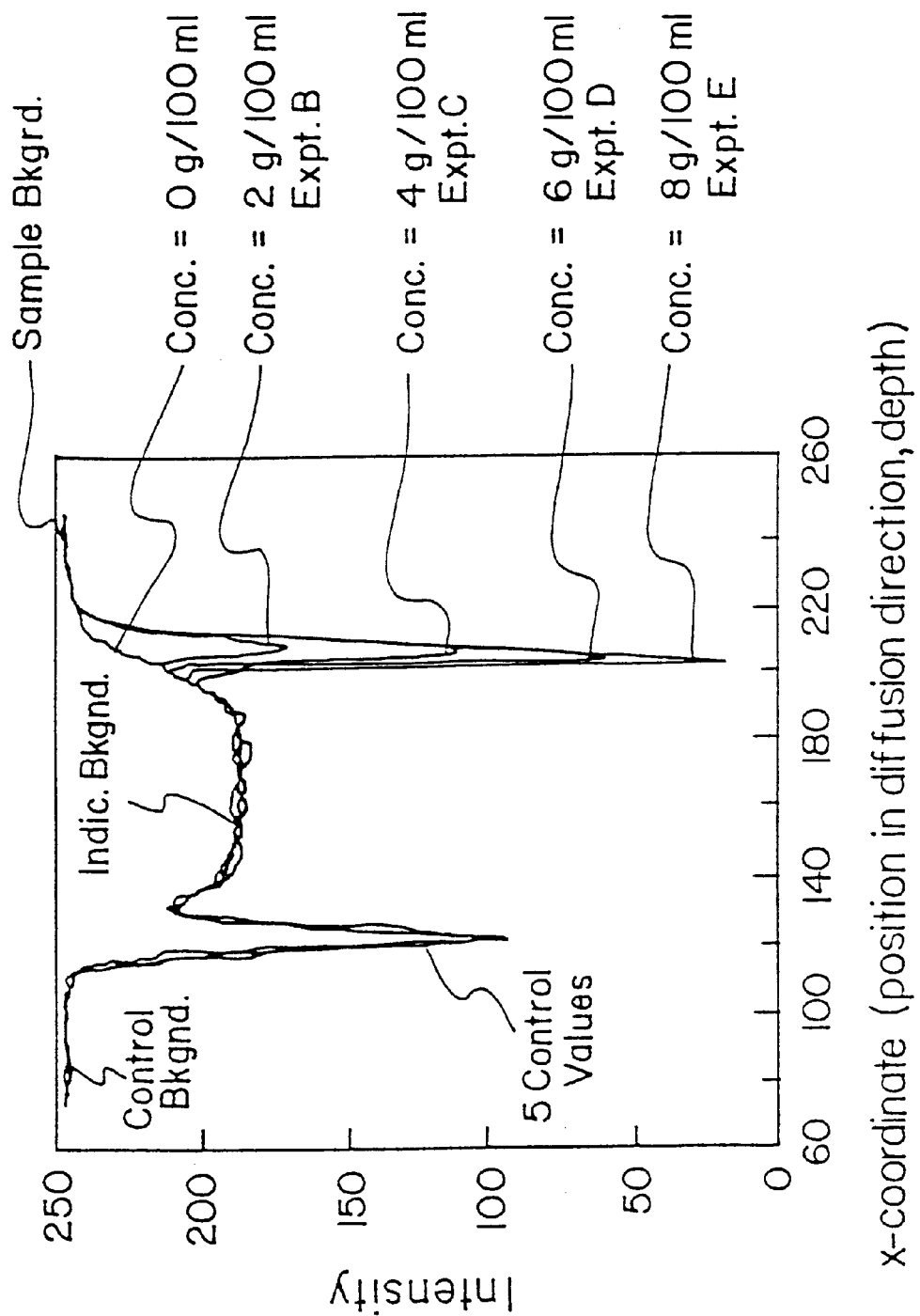
FIG. 9 is a graph of fluorescence intensity versus x-coordinate (position in the diffusion direction) of five experiments, wherein the sample stream contained 0, 2, 4, 6, and 8 g human serum albumin (HSA)/100 mL buffer, respectively. Also shown in this graph is the fluorescence of control streams containing 3.8 g HSA/100 ml buffer.

The fluorescence data shown in these photographs was recorded and graphed quantitatively, as shown in Table 1 and FIG. 9.

TABLE 1

| Expt. | [HSA] | Control Background | x-coor. Control | Fluorescence Control[1] | Indic. Background | x-coor. Sample | Fluorescence Sample[2] | Sample Background |
|---|---|---|---|---|---|---|---|---|
| A | 0   | 247.41 | 123 | 117.91 | 188.35 | 181 | 187.85 | 246.52 |
| B | 2.0 | 246.50 | 122 | 105.73 | 185.87 | 207 | 176.45 | 246.11 |
| C | 4.0 | 247.76 | 123 | 118.03 | 187.65 | 207 | 124.15 | 247.71 |
| D | 6.0 | 247.01 | 122 | 101.94 | 188.24 | 206 | 72.67  | 247.85 |
| E | 8.0 | 247.69 | 124 | 116.67 | 189.29 | 205 | 39.85  | 247.21 |

[1] Fluor. Cntl. refers to the fluorescence detected in the control analyte detection area, i.e., at the interface of the control stream with the indicator stream.
[2] Fluor. Sample refers to the fluorescence detected in the sample analyte detection area, i.e., at the interface of the sample stream with the indicator stream.

FIG. 9 is a graph of fluorescence intensity versus x-coordinate, which is the position in the diffusion direction (depth) of the flow channel. (The numbers on the y-axis decrease as the fluorescence increases as a result of a software artifact: brighter (more fluorescence) areas are labeled with lower pixel intensity numbers, and darker (less florescence) areas are labeled with higher pixel intensity numbers.) In the upper left portion of the graph, the background fluorescence of the control streams is shown: it is very small, and substantially the same for each of the five cases. The large peak/dip at position 122–124 shows the fluorescence of the control stream, which contains 3.8 g HSA/100 mL buffer: the fluorescence is strong and substantially the same for each of the five cases. (Three data points are averaged to obtain each data value shown in Table 1.) The shallow peak/dip at about position 130–190 shows the background fluorescence of the indicator stream: it is moderate, varying from about 185 to 189, and substantially the same for each of the five cases. The four peaks at positions 207, 207, 206 and 205 show the fluorescence of the samples containing concentrations of HSA of 2, 4, 6, and 8 g/100 mL, respectively. These correspond to Experiments A, B, C, D, and E, respectively. The intensity values are 176.45, 124.15, 72.67, and 39.85, respectively. At the upper right portion of the graph the background fluorescence of the sample streams is shown: it is very small, and substantially the same for each of the five cases.

Example 3

Figure 10:
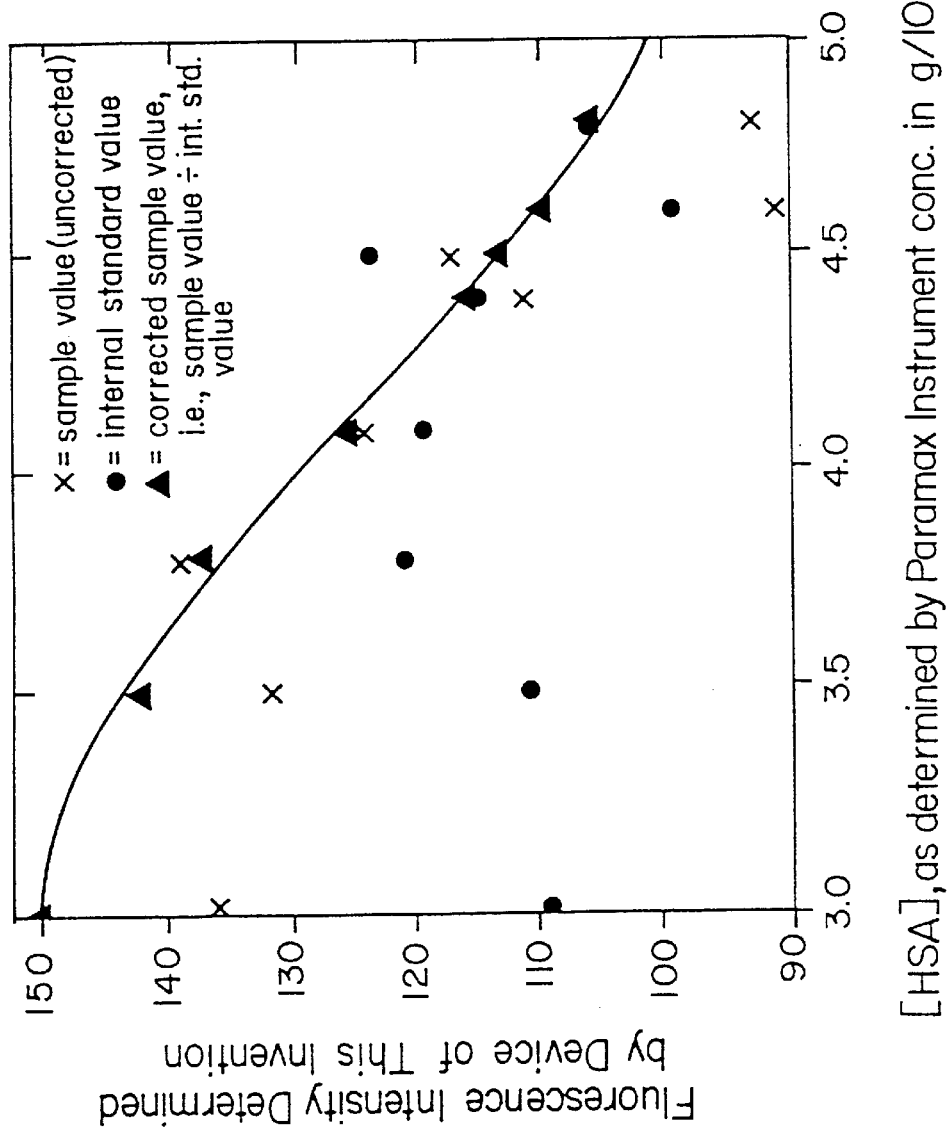
FIG. 10 is a graph of fluorescence intensity versus concentration of HSA (as determined by an art-known device) for both raw (uncorrected) data and corrected data. Also included is a calibration curve.

Determining the Concentration of HSA in Eight Clinical Samples and Correcting by Internal Standards FIG. 10 is a graph of fluorescence intensity versus concentration of HSA from eight clinical samples of human whole blood. The reference T-sensor was calibrated by measuring the fluorescence intensity of calibration streams with known concentrations (2, 4, 6, and 8 g/100 mL buffer) of HSA. The indicator stream was made according the procedure described in Example 2. The calibration curve is shown in FIG. 10 as a dark curve. Next the fluorescence of each of the eight clinical samples was measured and graphed (shown as x) in FIG. 10. While measuring these data, internal standard streams containing 3.8 g HSA/100 mL buffer were run and measured and graphed (shown as circles) in FIG. 10. The fluorescence intensity from the sample streams was divided by the fluorescence intensity of the internal standard streams, yielding the corrected values, shown in FIG. 10 as triangles.

FIG. 10 shows that the corrected values fall closer to the calibration line, than do the uncorrected (raw) data. This illustrates one of the advantages of the device and method of this invention which provide for correction of experimental conditions by the use of internal standard streams. Paramax is an instrument known to those skilled in the art and employs optical absorbance measurements and automated mixing of samples and reagents to determine the concentration of analytes in clinical samples.

Example 4

Quality Control of Flow Rate by Graphing a Levy-Jennings Plot

Figure 11:
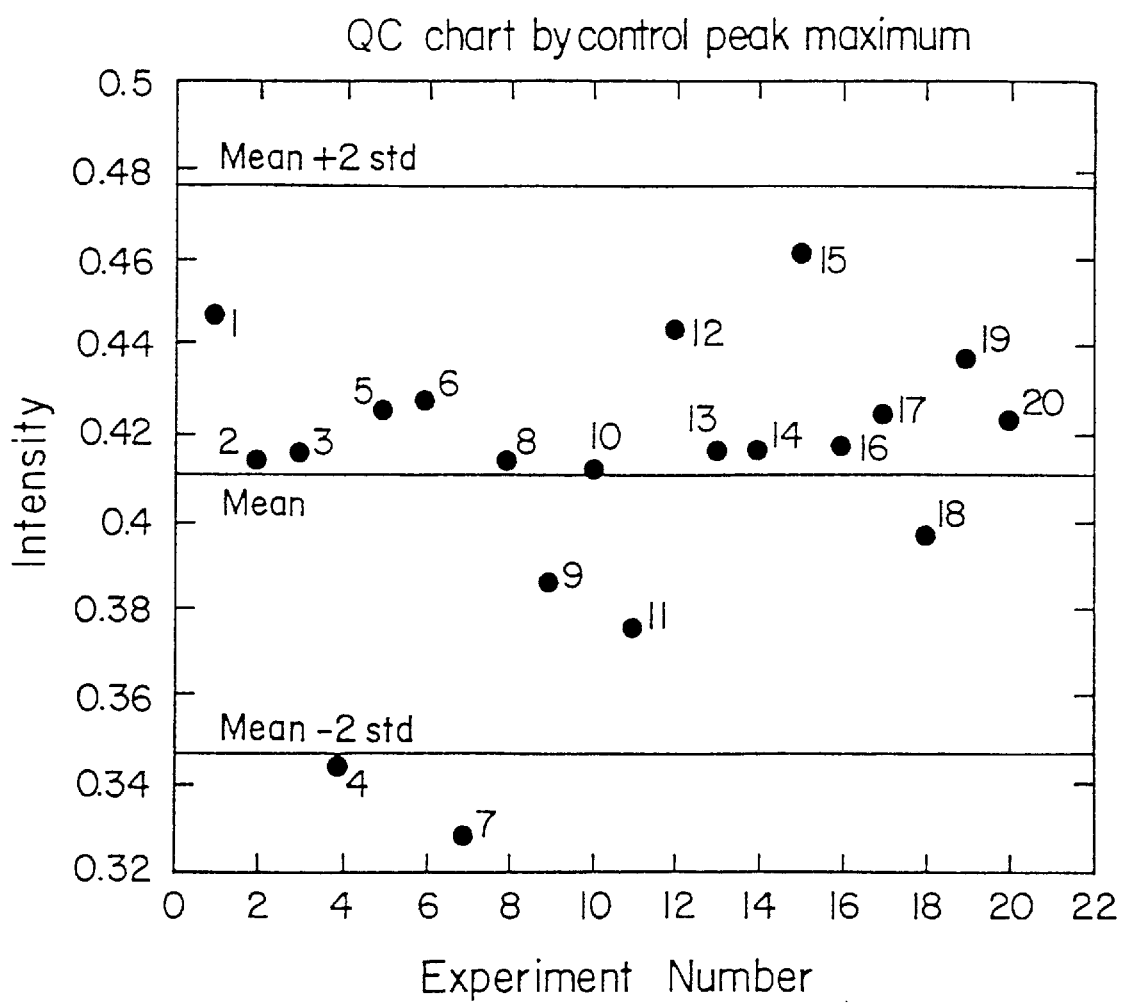
FIG. 11 is a QC chart (Levy-Jennings) plot of fluorescence intensity of a control stream (control analyte detection area) for 20 different experiments.

FIG. 11 is a QC chart (Levy-Jenning) of data collected from a device of this invention to demonstrate the quality control function of the device. Fluorescence intensity was plotted on the y-axis and the experiment number was plotted on the x-axis. FIG. 11 plots 20 control streams and illustrate that 18 of the 20 fall within two standard deviations of the mean, i.e., target value for concentration of HSA. Only experiments 4 and 7 yielded values which fell outside two standard deviations of the target value. This type of chart is useful for checking flow rate and/or reagent variations, lamp source variations and other variations in system parameters of the streams in the device of this invention. If the measured control values fall within two standard deviations of the target value (or whatever range is precise enough for a given project), these parameters are properly controlled for.

We claim:

1. A device for detecting the presence or determining the concentration of analyte particles in a sample stream comprising:
   a) a laminar flow channel;
   b) at least three inlet means in fluid connection with said laminar flow channel for respectively conducting into said laminar flow channel (1) an indicator stream, (2) a sample stream, and (3) a reference stream;
   c) wherein said laminar flow channel has a dimension sufficiently small to allow laminar flow of said streams adjacent to each other and a length sufficient to allow analyte particles to diffuse from at least one stream selected from the group consisting of said sample stream and said reference stream into the indicator stream to form at least one detection area; and
   d) outlet means for conducting said streams out of said laminar flow channel.

2. A device of claim 1 wherein said outlet means conducts said streams out of said laminar flow channel in a single mixed stream.

3. A device of claim 1 further comprising detecting means positioned relative to said flow channel such that said detecting means can detect a change in a detectable property in at least one of said streams.

4. A device of claim 3 wherein said detecting means comprise components selected from the group consisting of a charge coupled device camera, a diode array detector, a fluorescence detector, and an electrochemical detector.

5. A device of claim 1 further comprising inlet means for conducting at least one additional reference or sample stream in laminar flow contact with said indicator stream.

6. A device of claim 1 further comprising means for dividing said indicator or sample stream into at least two separate streams and conducting said separate streams into said laminar flow channel.

7. A device of claim 1 further comprising a plurality of laminar flow channels in fluid communication with an indicator stream channel and means for conducting portions of an indicator stream from said indicator stream channel into laminar flow with separate sample or reference streams in said laminar flow channels.

8. A device of claim 1 further comprising means for conducting at least two streams, each made up of at least two streams in laminar flow with each other, into parallel laminar flow in said laminar flow channel.

9. A method for detecting the presence or determining the concentration of analyte particles in a sample stream, comprising:
   a) conducting said sample stream into a laminar flow channel;
   b) conducting an indicator stream, said indicator stream comprising an indicator substance which indicates the presence of said analyte particles by a change in a detectable property when contacted with particles of said analyte, into said laminar flow channel, whereby said sample stream and said indicator stream flow in adjacent laminar flow in said channel;
   c) conducting a reference stream, comprising a constant concentration of 0 or greater of reference particles into said laminar flow channel, whereby said reference stream flows in a laminar stream adjacent to said indicator stream;
   d) allowing analyte particles to diffuse into said indicator stream;
   e) allowing reference particles to diffuse into said indicator stream; and
   f) detecting the presence or determining the concentration of said analyte and reference particles in said indicator stream.

10. The method of claim 9 wherein the reference stream contains a concentration of analyte particles which is greater than zero.

11. The method of claim 9 wherein two indicator streams are conducted into said laminar flow channel in adjacent laminar flow to said sample stream.

12. The method of claim 9 wherein two reference streams are conducted into said laminar flow channel in adjacent laminar flow to said indicator stream.

13. A method of claim 9 wherein said reference stream is a control stream.

14. A method of claim 9 wherein said reference stream is an internal standard stream.

15. A method of claim 14 wherein said internal standard stream contains reference particles different from said analyte particles.

16. A method of claim 14 wherein said internal standard stream contains reference particles the same as said analyte particles.

17. A method of claim 9 wherein said reference stream is used both as a control stream and as an internal standard stream.

18. A method of claim 9 wherein said reference stream is used as a calibration stream.

19. A method of claim 9 wherein the detectable property is selected from the group consisting of absorbance, chemiluminescence and fluorescence.

20. A method of claim 9 wherein the indicator substance is immobilized on a particulate substance carried within the indicator stream.

* * * * *